(12) United States Patent
Treat et al.

(10) Patent No.: US 7,997,847 B2
(45) Date of Patent: Aug. 16, 2011

(54) AUTOMATED ROBOTIC SYSTEM FOR HANDLING SURGICAL INSTRUMENTS

(75) Inventors: Michael R. Treat, New York, NY (US); David Michael Brady, New York, NY (US); Russell Baker, Sunnyside, NY (US); Jack M. Kaplan, Princeton, NJ (US); David Berk, East Brunswick, NJ (US)

(73) Assignee: Robotic Systems & Technologies, Inc., Bronx, NY (US)

( * ) Notice: Subject to any disclaimer, the term of this patent is extended or adjusted under 35 U.S.C. 154(b) by 0 days.

(21) Appl. No.: 12/747,036

(22) PCT Filed: Dec. 10, 2008

(86) PCT No.: PCT/US2008/086252
§ 371 (c)(1),
(2), (4) Date: Aug. 20, 2010

(87) PCT Pub. No.: WO2009/076452
PCT Pub. Date: Jun. 18, 2009

(65) Prior Publication Data
US 2011/0005342 A1      Jan. 13, 2011

Related U.S. Application Data

(60) Provisional application No. 61/012,683, filed on Dec. 10, 2007, provisional application No. 61/074,268, filed on Jun. 20, 2008, provisional application No. 61/113,646, filed on Nov. 12, 2008.

(51) Int. Cl.
*A61B 19/00* (2006.01)
*A61G 13/10* (2006.01)
*B65G 69/20* (2006.01)
*B25J 9/00* (2006.01)
*G01M 99/00* (2011.01)

(52) U.S. Cl. .............. 414/222.01; 73/788; 73/865.8; 73/865.9; 356/72; 356/73; 356/237.1; 356/237.2; 356/69; 356/426; 414/222.02; 414/754; 414/758; 414/806; 414/816; 702/81

(58) Field of Classification Search ............ 73/788, 73/865.8–865.9, 862.541; 128/897–898; 209/538, 555, 583, 587, 939; 356/69, 72–73, 356/237.1–237.3, 426, FOR. 100; 414/222.01, 414/222.13, 222.02, 806, FOR. 101, FOR. 105; 700/114–115, 117, 214–215, 223–225; 702/81, 702/182–184, FOR. 135
See application file for complete search history.

(56) References Cited

U.S. PATENT DOCUMENTS
3,343,669 A * 9/1967 Loran ............... 206/63.5
(Continued)

OTHER PUBLICATIONS
International Search Report dated Jul. 9, 2009, which was issued for PCT/US2008/086252.

*Primary Examiner* — Thomas P Noland
(74) *Attorney, Agent, or Firm* — Katten Muchin Rosenman LLP

(57) ABSTRACT

Systems and methods that process a plurality of surgical instruments for cleaning and/or packaging. A device identifies a robot-ready insert having a predetermined configuration for accepting at least one type of surgical instrument. The surgical instruments are identified and oriented according to type using an automated apparatus. Specialized tools are also provided for automatically opening and closing surgical instruments, flipping instruments and assisting in the processing and maintenance of surgical instruments. The automated apparatus then places each of the surgical instrument types in one or more predetermined areas of the insert, configured to accept a predetermined set of surgical instrument types.

11 Claims, 23 Drawing Sheets

U.S. PATENT DOCUMENTS

| | | | |
|---|---|---|---|
| 4,043,754 A * | 8/1977 | Sklar | 422/560 |
| 4,643,303 A * | 2/1987 | Arp et al. | 206/370 |
| 6,347,460 B1 * | 2/2002 | Forrer et al. | 33/626 |
| 6,827,212 B2 * | 12/2004 | Reaux | 206/372 |
| 7,142,118 B2 | 11/2006 | Hamilton et al. | |
| 7,164,968 B2 | 1/2007 | Treat et al. | |
| 7,518,502 B2 * | 4/2009 | Austin et al. | 340/539.1 |
| 7,896,869 B2 * | 3/2011 | DiSilvestro et al. | 128/898 X |
| 2005/0038556 A1 | 2/2005 | Gagnon et al. | |
| 2005/0215888 A1 * | 9/2005 | Grimm et al. | 600/426 |

* cited by examiner (A)

(B)

(C)

(D)

(E)

120
AUTOMATED ROBOTIC SYSTEM FOR HANDLING SURGICAL INSTRUMENTS

RELATED APPLICATIONS

The present application claims the benefit of U.S. provisional patent application Nos. (1) 61/012,683, filed Dec. 10, 2007, (2) 61/074,268, filed Jun. 20, 2008, and (3) 61/113,646, filed Nov. 12, 2008, each of which are incorporated by reference in their entirety herein.

TECHNICAL FIELD

The present disclosure relates to systems, methods and processes for robotically processing instruments, and more particularly to robotic systems for handling and processing surgical instruments in sterile supply environments and the like.

BACKGROUND INFORMATION

Used surgical instruments and related medical devices are typically handled by a Central Sterile Supply (hereafter "CSS") department within a hospital or other related medical service facility, and is considered one of the most important service centers of a hospital. The CSS department typically processes used surgical instruments, and other types of reusable medical devices, from a "dirty" or contaminated state and returns them to a sterile state. Turning to FIG. 4, a conventional CSS process is illustrated. Containers of instruments are received from a "dirty" side of CSS, where the instruments are unloaded, hand washed 401, and cleaned ultrasonically 402 and disinfected 403. Once cleaned, the instruments are counted 404, sorted 405, and packed 406 prior to placement in a steam sterilizer or autoclave 407. Once a container has been removed from the autoclave, it is then considered sterile and ready to be used.

An exemplary container described in connection with FIG. 4 is further illustrated in FIG. 3. Container 317 is typically made of metal, having the dimensions 18"(L)×12"(W)×6" (D), for holding dirty instruments arriving from an operating room (OR) or other clinical facility. While there are several sizes of containers, all are sized within certain limits to be able to fit into a standard washing and sterilizing machines. Container 317 has a cover that is latched in place at each end of the container by a secure and tamper proof mechanism. Containers 317 is further equipped with some sort of identifying label or tag 321 on an exterior surface. Tag 321 can be a printed label, barcode or a radio-frequency identification (RFID) tag. Tag 321 is used to associate the container with a particular count sheet listing its intended contents.

Container 317 also includes a tray 318, that fits inside container 317. Tray 318 is typically made of perforated steel or other suitable material, to allow fluids and other material to pass through during the various stages of the sterilization process. Tray 318 may be configured to accept dividers or inserts to organize or separate tools, and/or hold the tools in a particular fashion. Nevertheless, many trays in current use do not have inserts, but use stringers 320 as their prime organizational tool. As can be seen from the illustration in FIG. 3, stringer 320 is a U-shaped rod that is typically made of steel. The length of the "U" for stringer 320 runs through both finger loops of a suitable instrument, such as scissors or hemostats. Typically, stringer 320 is equipped with a means for closing off the top of the "U" to prevent the instruments from sliding off. When preparing instruments 319 for sterilizing, trays 318, inserts (not shown), stringers 320 and instruments 319 are placed inside of container 317 or alternately wrapped up in a special wrapping paper-like material.

As is known in the art, handheld surgical instruments 319 are typically made of stainless steel, though other materials may be equally suitable. Standard instruments include scissors, tweezer-like graspers, latching graspers ("hemostats"), and retractors of various shapes.

A large number of surgical instruments also contain a ratchet lock, typically with instruments having a finger ring configuration. Ratchets are located between each finger ring and the shank. The ratchets are smooth on one side and toothed on the other, and are often configured to have three "teeth", where, when the instrument is closed, the toothed sides interlock. Thus, to close the instrument, the finger rings are drawn together and the jaws of the instrument meet before the teeth of the ratchet lock. Once the jaws meet, force must be applied to overcome the strength of the shafts and engage the teeth. Engagement of each successive tooth requires greater force. To open the instrument, first the ratchet must be disengaged. This is done by forcing the finger rings in the directions normal to their respective smooth sides of the ratchet. Once the teeth are separated, the finger rings should be moved apart to prevent reengagement of the teeth upon relaxation of the force.

Referring back to FIGS. 3 and 4, a conventional sterile supply process will be described in greater detail below. As an overview, the CSS process may be summarized chronologically as follows:

unload tray or container from the operating room (OR);
identify instruments;
open the instruments;
clean the instruments by hand;
process tray through ultrasonic cleaner;
flip the orientation of instruments as required;
arrange the instruments so they can be properly cleaned in the washer/disinfector;
process tray through washer/disinfector;
inspect for cleanliness;
inspect for mechanical integrity (i.e. no parts chipped, bent, missing or damaged);
inspect for functionality;
pull defective or unclean instruments;
lubricate appropriate equipment;
sharpen appropriate equipment;
demagnetize appropriate equipment;
replenish missing or defective instruments;
sort instruments and/or equipment;
count instruments and/or equipment;
pack appropriate instruments back onto stringers and/or tray;
document instruments and/or equipment on count sheet;
wrap the tray; and
update the hospital inventory system.

After a surgical procedure, dirty instruments are sent to CSS with the intention of sterilizing and repackaging them for future use. Thus, the first step in the sterilization process is decontamination. Typically, a department worker opens a container and finds a tray with dirty, disorganized instruments. Each instrument is then manually washed or scrubbed (401). The purpose of this manual process is to physically remove deposits and to break up biofilms (such as dried blood) that may be adherent to the instruments.

At this point, the looped instruments are either thrown haphazardly back into the tray in an extreme open position, or they are placed on an extra wide stringer (320) that holds the instruments in the extreme open condition (i.e. as far as the instrument is physically capable of opening). The purpose of having them open is to expose the inner surfaces of the box lock hinge as much as possible, for cleaning and washing purposes. Other instruments such as retractors, which do not require opening, may also be thrown in at this point.

After the hand cleaning, the instruments proceed through a variety of rinsing and soaking procedures or baths. These baths may include ultrasonic cleaners or enzymatic solutions (402).

The instruments are then placed in a washer/disinfector (403), essentially a dishwasher for instruments where the instrument is cleaned by water impingement and detergent. These special-purpose dishwashers have a rotating spray bar which emits high pressure water and detergent spray to clean the instruments by impingement of the water jets on the instrument surfaces. It is optimal to have the looped instruments held in a wide open stance for this step to expose the critical locations on the instrument which may otherwise be obscured from the water jets.

When the instruments leave the washer/disinfector, they are considered decontaminated. Further processing continues on what is called the "clean" side of CSS (see FIG. 4). Here the instruments are inspected, counted 404, sorted 405, and repacked 406 into their containers. At this point, instruments are inspected for damage and to ensure that they are functioning properly. Thus, for example, a looped instrument's hinging mechanism must move freely, and cutting tools must be sufficiently sharp. Any broken or damaged instruments should be pulled from the set and either discarded or sent for maintenance. Some instruments also require routine maintenance such as lubrication, sharpening, or demagnetizing. These simple maintenance functions may be performed by CSS personnel at this time.

During the count and sort process (404, 405), the instruments in the container are compared to its count sheet. A count sheet specifies the type and quantity of each instrument to be included in the container. The count generated in CSS will form the basis for the count in the operating room (OR). During a procedure the surgical staff must maintain an accurate count of all the instruments to ensure none are inadvertently left behind in the patient. A mistake in the original count from CSS can significantly complicate the count in the OR. For example, an undercount in CSS can contribute to an instrument being erroneously left in the body cavity. On the other hand, an over-count can contribute to a false alarm, giving the erroneous appearance that an instrument is missing. Accordingly, the surgical team must search for the non-existent instrument, prolonging the procedure and the time the patient is under anesthesia.

Many CSS facilities still rely on paper for their count sheets. CSS facilities that are beginning to incorporate automated systems utilize software and/or instrument barcodes to help automate the process. Nevertheless, in either case, conventional CSS processes are still time consuming and error prone tasks.

As part of the sorting process, looped instruments are manually placed on a standard width stringer, so that similar instruments are adjacent to one another and preferably arranged largest to smallest in size. The standard width stringer holds the instruments in a nearly closed but un-ratcheted position, which is referred to in the art as a "soft" close. The non-looped instruments, such as retractors, are arranged on the bottom of the tray. The stringer full of instruments is placed into the tray, and the tray is placed into a container. The CSS worker will typically sign the count sheet and place it into the container with the tray. The container is then latched and ready for the sterilization process as mentioned above.

For CSS systems utilizing automated processes, a robotic automation mechanism is programmed and configured to manipulate relevant objects. Examples of such robotic systems may be found in U.S. Pat. No. 7,164,968, titled "Robotic Scrub Nurse," issued Jan. 16, 2007, which is incorporated by reference in its entirety herein. Under such systems, robotic manipulations for a given process must handle objects in a prescribed manner, and often run into situations where the manner of manipulation is beyond the means of the robot. In such cases, additional devices are required in order to achieve these goals. A device designed for such a purpose is said to be robot-ready. Additionally, there are increasing varieties of surgical instruments having different sizes, shapes, and characteristic features. Certain instruments may be found in different states (e.g., open, closed, upside-down) over the course of the sterile supply process. Accordingly, it is desirable to have a system and method for handling various types of instruments regardless of state, and to be able to transfer the instruments between states.

SUMMARY

As such, an exemplary system and method is disclosed for processing a plurality of surgical instruments for cleaning and/or packaging. The system includes a device for identifying a robot-ready insert, wherein the insert contains a plurality of surgical instruments in one or more predetermined areas, and each area of the insert is configured to accept a predetermined set of surgical instrument types. Each of the plurality of surgical instruments is then removed from the predetermined areas using an automated apparatus, preferably a robotic arm. An apparatus is also provided for optically or electrically identifying each of a plurality of surgical instruments. Each of the plurality of surgical instruments is then processed so as to perform various functions related to cleaning and/or packaging. An automated apparatus, preferably a robotic arm, then orients each of the identified surgical instrument, and places each of the surgical instruments in one or more predetermined areas of the insert, where each area of the insert is configured to accept a predetermined set of surgical instrument types.

Specialized tools are also provided for automatically opening and closing surgical instruments, flipping instruments and assisting in the maintenance of surgical instruments.

Under additional and/or alternate embodiments, a robotic system and corresponding methods are disclosed for performing the functions of the CSS Department of a hospital, as well as additional functions relating to trafficking surgical instruments from a point of use to a point of processing for re-use. The robotic system includes the following components: a robotic arm or other mechanism for physically handling and moving about the surgical instruments, a machine-vision system to assist in locating and identifying these items, and a software system that incorporates artificial intelligence capability so that the system may perform its functions autonomously after receiving guidance from a human operator.

The aforementioned robotic system also performs one or more of the following functions: unload surgical instruments or other types of items used in surgery from a container, and then clean, identify, inspect, count, sort, and package the instruments and other items. The system may perform other functions including opening, closing, lubricating, sharpening, and/or demagnetizing instruments or items, as well as preparing the container of instruments for sterilization by wrapping it.

The robotic system may further perform functions related to reading a bar code or other tag device on individual surgical instruments or on tray inserts of surgical instruments. Also, the robotic system may read and/or write RFID tag data or other read-write information device that may be affixed to a container of instruments or even to individual instruments. The robotic system would obtain and process such data as needed to describe details of individual instrument usage and history, as well as the detailed inventory or list of the instruments or items that have been packaged into the container.

Furthermore, the robotic system may be configured to interface with and update a hospital inventory system or database. Using the interface, the robotic system may communicate, process and/or update information regarding instruments or items that are lost, damaged, needing replacement, or other data regarding instrument usage (e.g., the number of times an instrument has been used). The robotic system may also be configured to prepare reports relating to instrument or item usage over time. The robotic system may also accept inputs from surgeons indicating preferences for contents of containers and may prepare containers with the instruments or items. Preferably, all of these functions of the robotic system are under the control of a software artificial intelligence that allows the system to perform its functions autonomously.

In addition to the robotic system, specially designed inserts for surgical instrument trays are disclosed. Under an exemplary embodiment, the inserts are configured for the organization of looped instruments, and are designed to encourage users of the system to use the described extra wide stringer method before the washer/disinfector cycle. The insert is further designed to ease the various loading and unloading processes. Use of the extra wide stringer increases the cleaning efficiency of the washer/disinfector and reduces the number of dirty instruments making it back to the operating room. Use of the extra wide stringer also simplifies the counting and sorting processes.

The aforementioned inserts maintain looped instruments in an orderly arrangement and enable an insert to be processed by a robotic CSS system. A simple easy to use design is necessary to bridge the human/robot interface, and usher in automation to an archaic system. The inserts also allow looped instruments to be presented to operating room staff in a more accessible manner.

Further still, additional accessory mechanisms or stations are disclosed that can be arrayed around the reach of an arm of the robotic system. The additional mechanisms are embodied as special purpose devices that accomplish exemplary tasks such as opening and closing of ratcheted instruments, vigorous mechanical roller brush or spray wash cleaning of instruments, lubricating hinges or joints, sharpening scissors, demagnetizing instruments, and performing certain physical tests on the instruments. Also, a special station for reading bar codes or laser etching bar codes onto the instruments may be provided, if required, as well as a station for reading and writing RFID tags.

Other objects, features, and advantages according to the present invention will become apparent from the following detailed description of certain advantageous embodiments when read in conjunction with the accompanying drawings in which the same components are identified by the same reference numerals.

DETAILED DESCRIPTION

Figure 1:
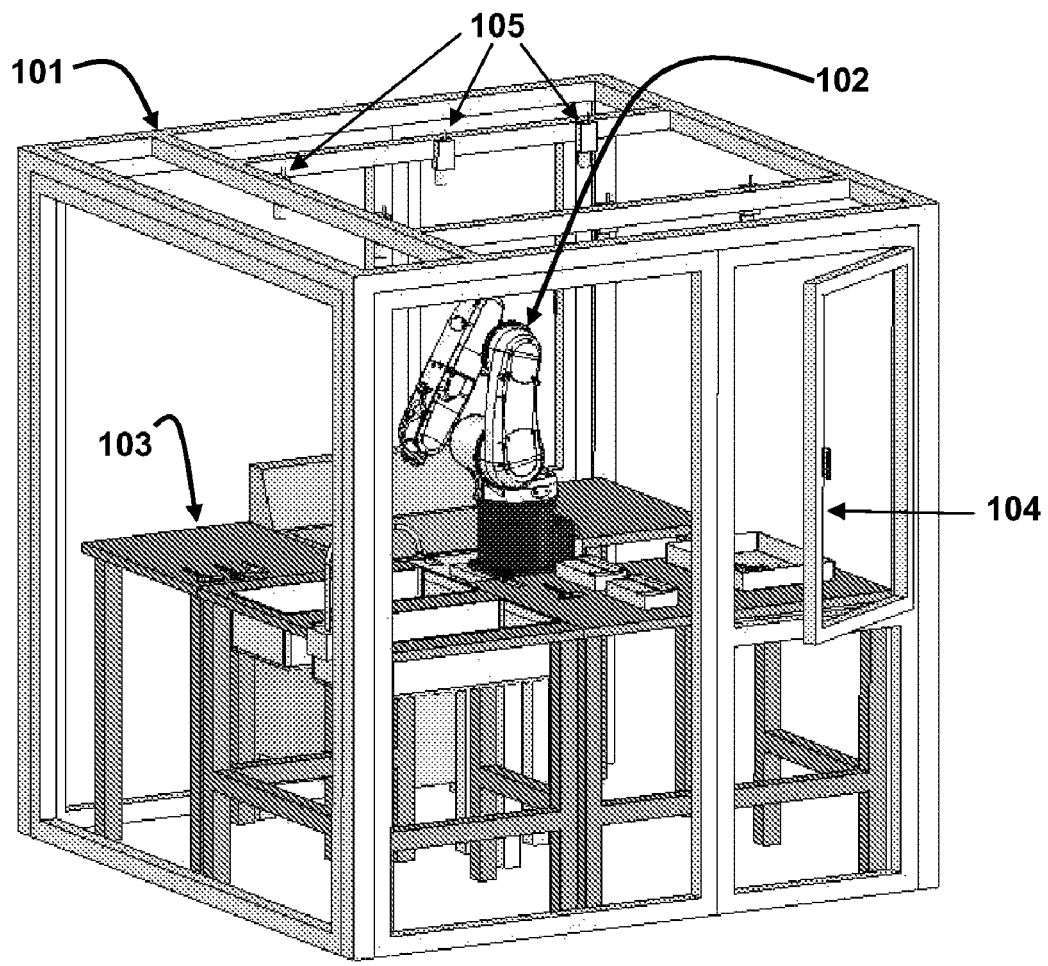
FIG. 1 illustrates a perspective view of a robotic workcell system under an exemplary embodiment.

FIG. 1 illustrates an automated, robotic CSS workcell system 100 under a preferred embodiment. System 100 comprises an enclosure 101 having one or more openings 104 for accessing a workspace surface 103. While the robotic workcell enclosure 101 is illustrated as a generally square, or rectangular shape, enclosure 101 could be designed with a cylindrical shape mimicking the robot's operational envelope 203. Additionally, the height of the enclosure could be minimized to allow vertical stacking of multiple robots in situations where floor space is at a premium.

Robotic arm 102 is preferably located in the center of the workspace surface 103, and is responsible for performing various manipulations to instruments and/or equipment described below. One example of a robotic arm suitable for use in system 100 is an Adept Viper™ s650 6-axis arm produced by Adept Technologies, Inc. Other suitable arms include "VS" or "VM" series 6-axis arms from DENSO Robotics, or Pro Six PS3 by Epson Robotics. It is also possible to design and build a custom robotic arm for this purpose. Other types of robotic arms may be used, including overhead gantry x-y-z Cartesian robots or SCARA-type robotic arms. Furthermore, more than one type of robotic arm may be employed in some embodiments of the full system.

Robotic arm 102 is equipped with a central computer control system (not shown) that is suitably programmed for directing operations for arm 102. The computer control system may be integrated directly into the arm itself, or may be located at a remote location. Arm 102 is also equipped with a special gripper for handling surgical instruments. In one embodiment, this gripper may be electromagnetic, but other means to handle the instruments including mechanical grippers and suction grippers may also be used. It is understood that many different types of gripper or grippers could be attached and even combined with each other on the basic arm in order to manipulate the surgical instruments.

Workspace surface 103 is configured to be of a suitable size to accommodate various instruments for identifying, inspecting and counting by system 100. Robotic arm 102 may be in a fixed position, or may be mounted on a moving track or sliding mechanism in order to extend its reach. In addition, the system 100 may alternately employ conveyor belts or vibrating tables on workspace 103 to move instruments from one location to another. The system may also employ special mechanisms to perform certain tasks such as opening or closing the instruments or even sharpening them as needed. The system also employs means for washing and lubricating the instruments. These means may be ultrasonic agitators loaded with baths of cleaning fluid to remove dried blood, etc. from the instruments. There may also be a bath of lubricating fluid into which the instruments may be dipped.

Examples of commercially available devices for maintaining instruments are the EdgeCraft ScissorPro™, which can be used as a sharpener. Bench-top demagnetizer from Electro-Matic Products Co. can be used for that demagnetization duty. A lubricating device would preferably comprise a solenoid-actuated plunger on a syringe or a small, motorized pump that would place a drop of oil on a predetermined spot such as the hinge joint of a scissors or hemostat.

As an important part of its functioning, system 100 employs a machine-vision system for identifying, inspecting, counting and sorting the instruments. Multiple machine-vision cameras 105 would typically be used, to obtain different perspectives on the instruments or to view different parts of the work-space. Cameras 105 may be situated on one side of the system enclosure 101, but are preferably installed to have two or more angular views of workspace 103. Examples of a type of camera suitable for system 100 includes a Fire-i™ Digital Camera manufactured by Unibrain, Inc., and other similar cameras satisfying the IIDC-1394 Digital Camera, V1.04 Specification. Additionally, system 100 may incorporate a barcode reader, or RFID tag reader and/or other means to identify individual instruments.

Machine-vision and other modalities provide data to the central computer control system to enable the computer to count and sort the instruments and to produce a detailed inventory of the number and type of instruments present in the container. The system software includes a reporting module to track all instruments, making note of defects, need to sharpen, or old items that may need to be pulled from service. If the instruments are individually marked, for example, by bar codes or RFID tags, then system 100 will track the number of cases in which a particular instrument has been used and therefore be able to decide if a particular instrument is in need of maintenance (i.e. sharpening) before it is returned to duty.

At the start of processing of a used tray, the system has the capability to use its robotic manipulator 102 and gripper to withdraw the instruments one by one from a used tray that has been brought down from the OR. At the end of the cleaning and inspecting process, system 100 also has the capability to place the instruments in a predetermined orderly fashion back into a clean tray. The entire system 100, including robotic arm, associated special mechanisms, washing facilities (see FIGS. 2A-B) and work area are enclosed in a large closed (not shown) cabinet with visual access, so that the CSS staff may observe the proper functioning of the system, but will also be shielded from accidental exposure to blood or bodily fluids that are present or the "used" instruments that are being processed. Additionally, the robotic arm 102 and other internal mechanisms of the system are implemented in such a way that they themselves may be washed down and disinfected by a set of spray jets located within the cabinet enclosure.

Figure 2A:
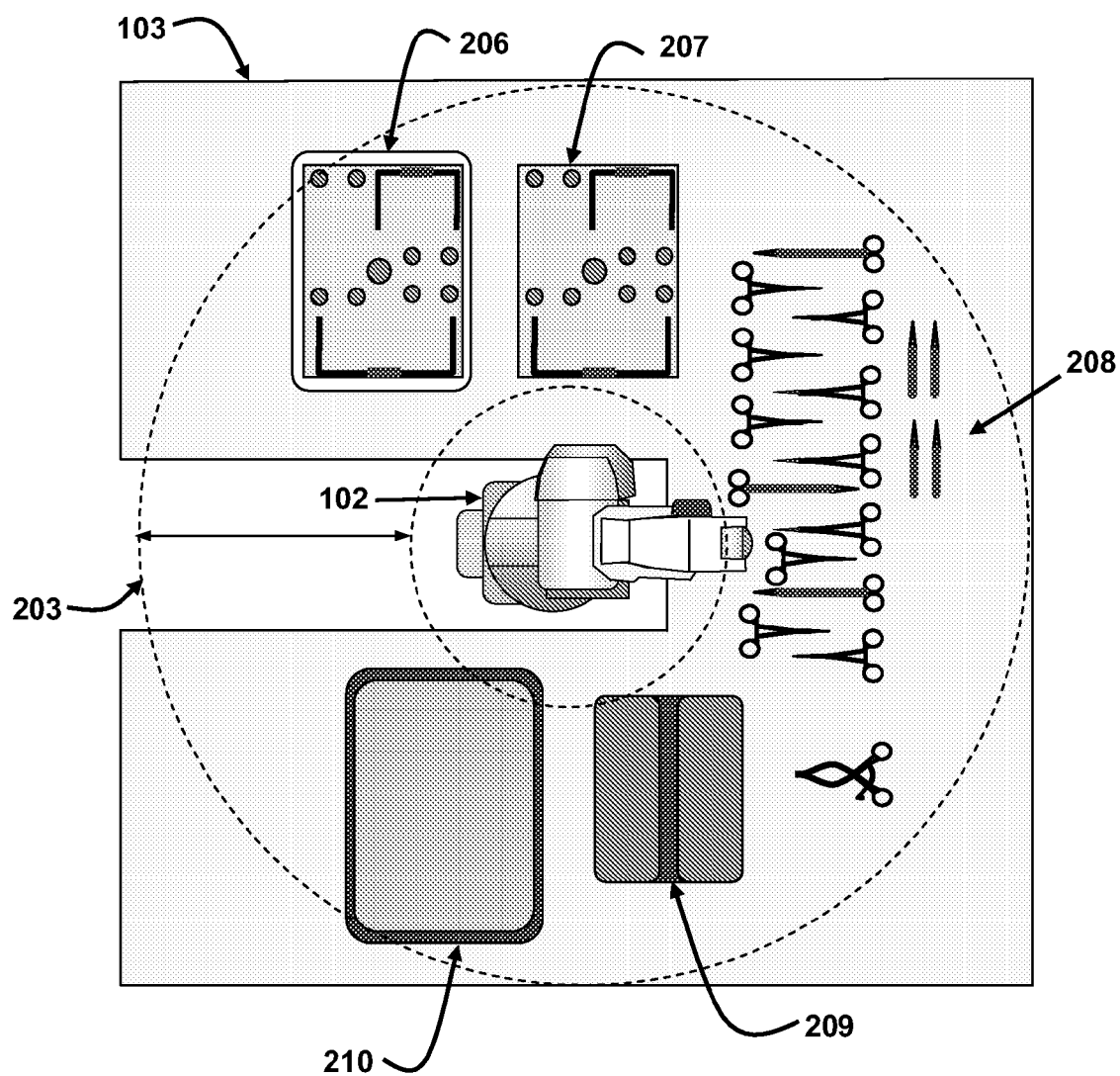
FIG. 2A illustrates a top view of the workcell system of FIG. 1, configured for dirty side processing under an exemplary embodiment.
Figure 2B:
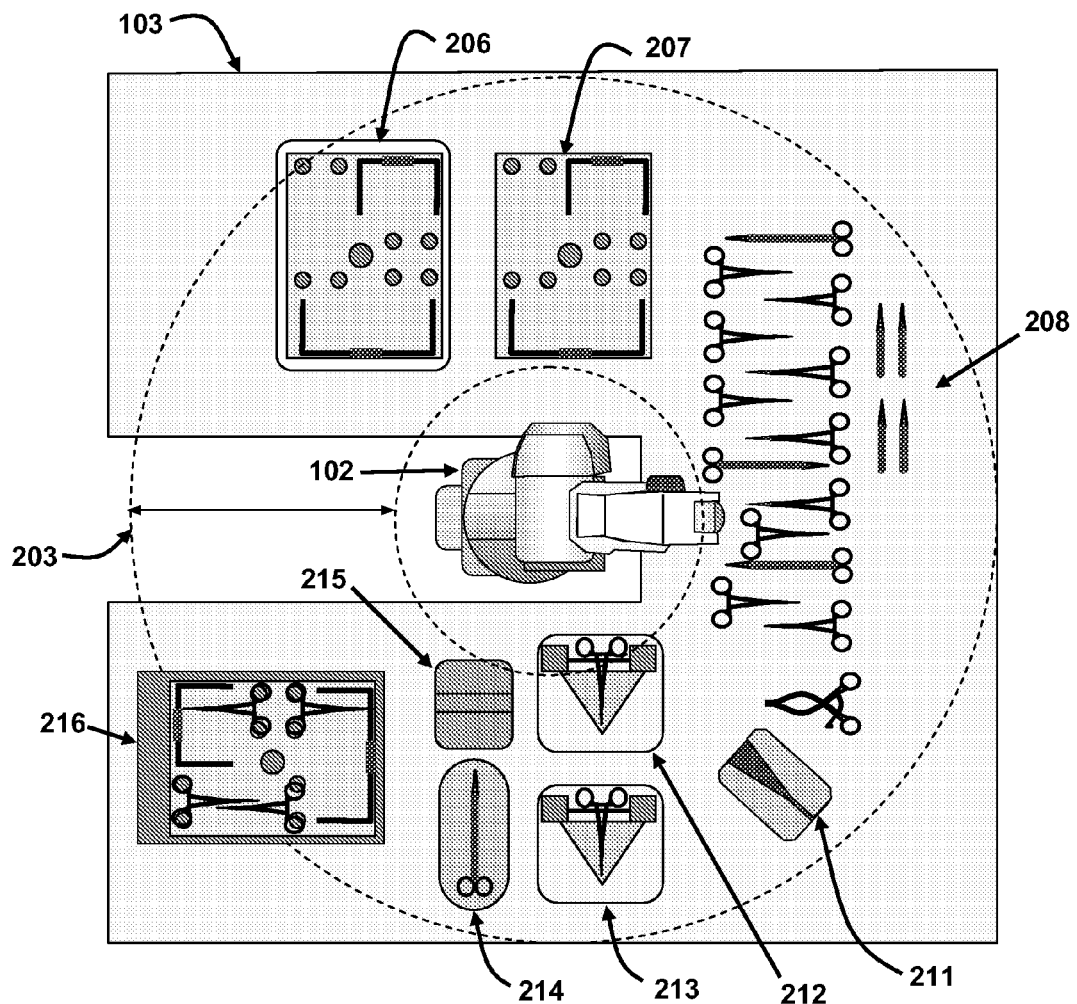
FIG. 2B illustrates a top view of the workcell of FIG. 1, configured for clean side processing under an exemplary embodiment.
Figure 3:
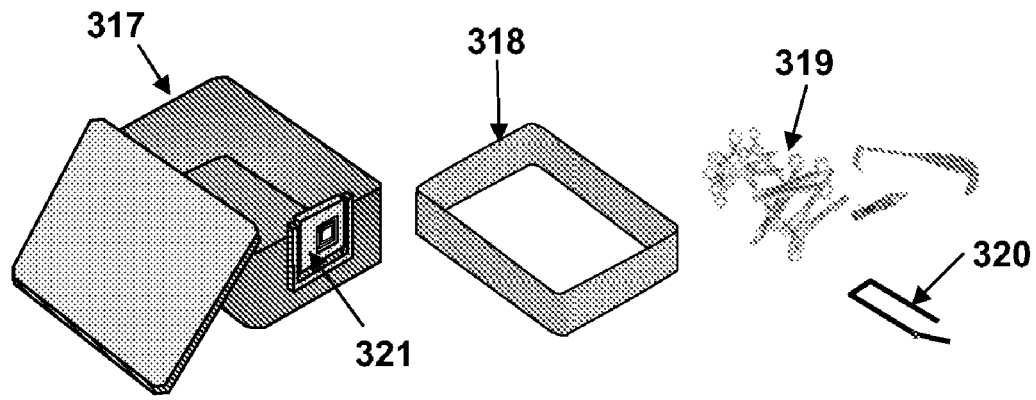
FIG. 3 shows components of a surgical container known in the art.

Exemplary top-down views of system workstation 103 are illustrated in FIGS. 2A and 2B. At the center of workstation 103 is a suitably programmed robotic arm 102 that preferably has 360° rotation with a lateral reach 203 throughout the workstation 103 to access and manipulate trays 206, robot-ready inserts 207, and instruments 208 as shown in FIG. 2A. In the examples of FIG. 2A and FIG. 2B, additional robot-ready accessories (209-216) may be introduced. Some examples of robot-ready accessories include, but are not limited to, an instrument washer 209, an ultrasonic cleaner 210, an instrument sharpener 211, an instrument opener 212, an instrument closer 213, a demagnetizer 214, a lubricator 215, and a storage cabinet 216.

Figure 15:
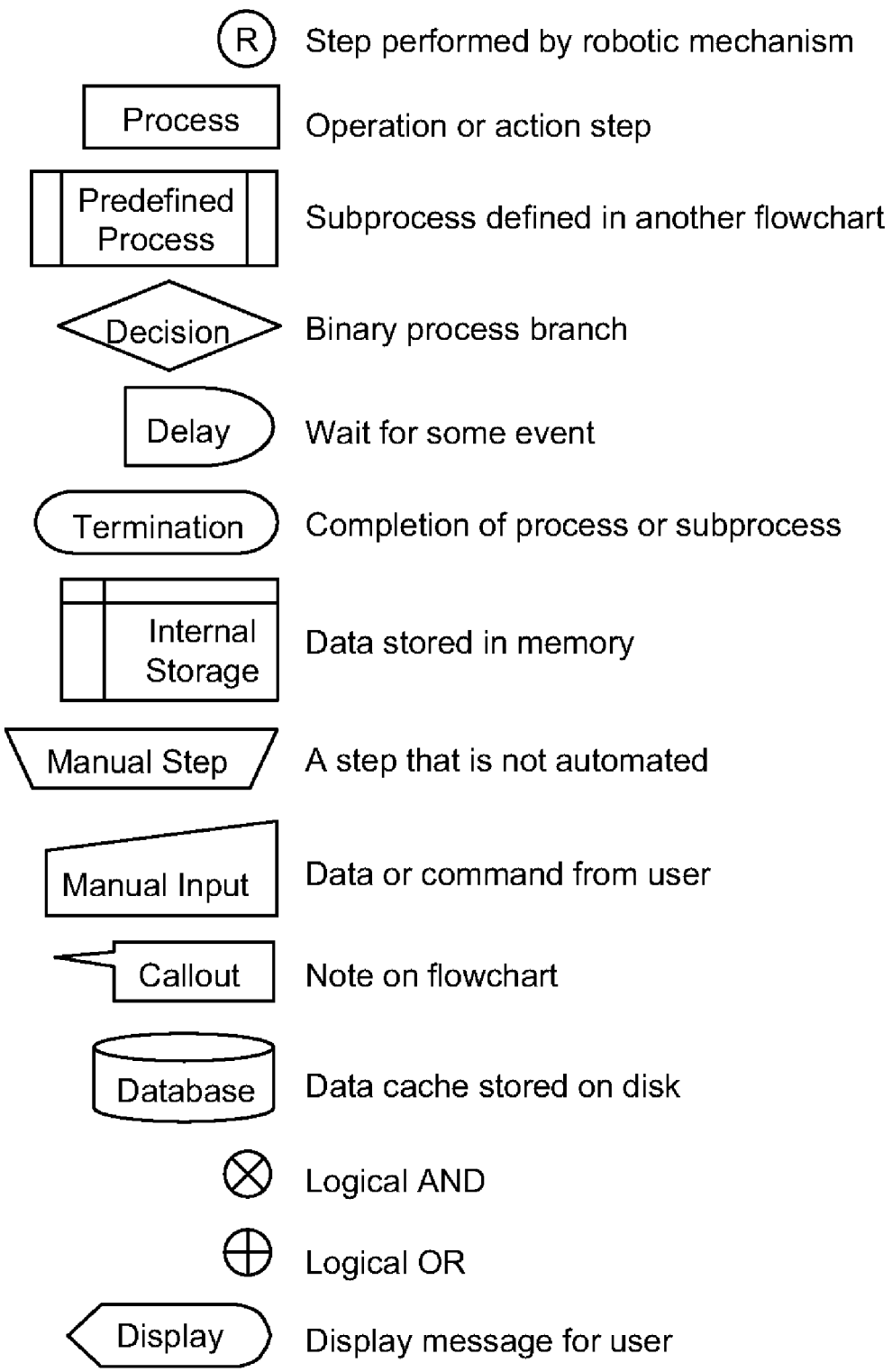
FIG. 15 shows a legend defining symbols used in the exemplary flowcharts illustrated in FIGS. 16-27, as they relate to the system shown in FIG. 1.
Figure 16:
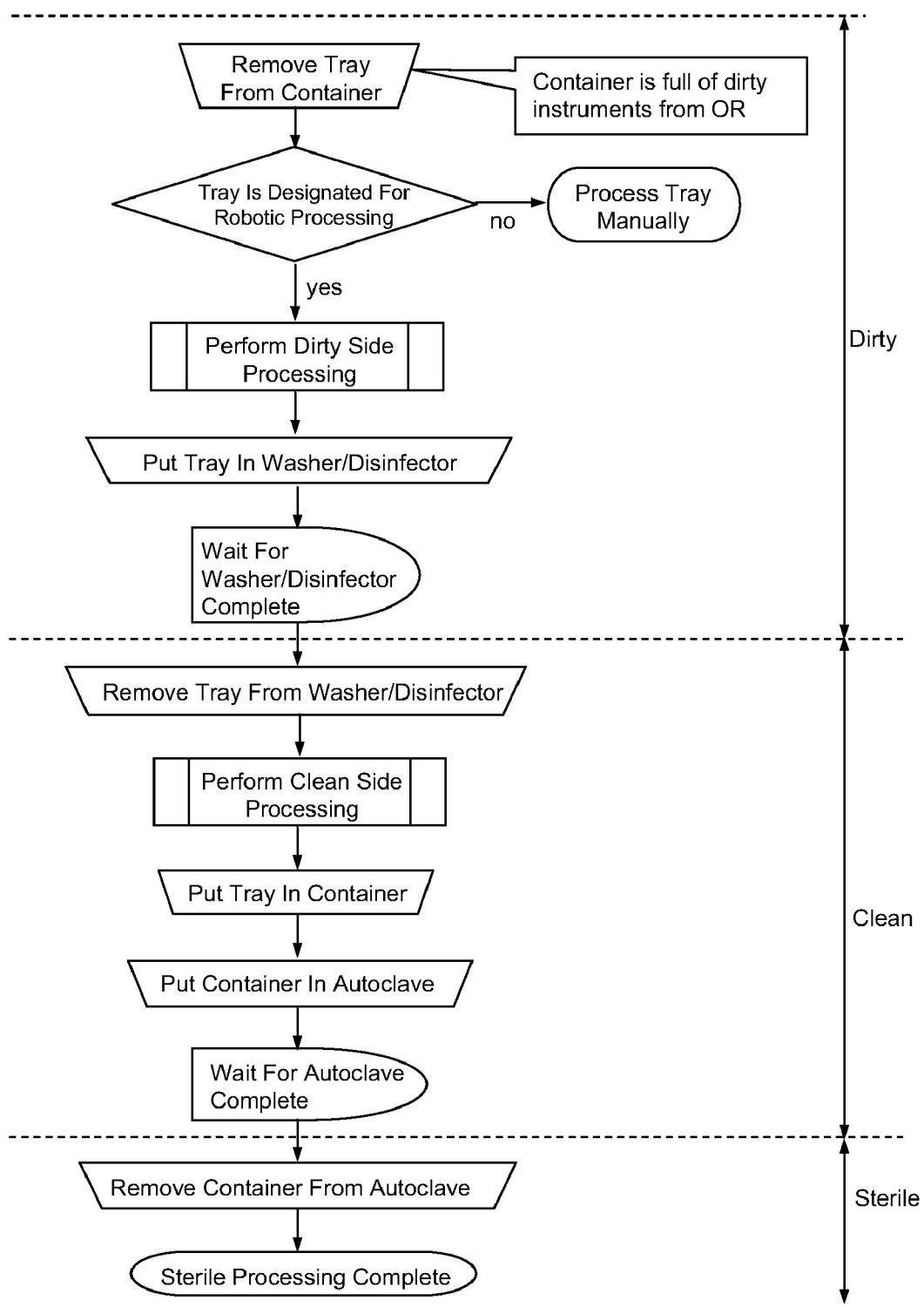
FIG. 16 is an exemplary flowchart for top-level processes.

An exemplary top-level process flow is shown in FIG. 16 (for reference, the legend for FIGS. 16-27 is shown in FIG. 15). When a dirty container of instruments from the operating room (or other clinical facility) enters the CSS, personnel remove the trays. Trays can be designated for robotic processing with a simple label, RFID tag, bar code, or other method. CSS Trays so designated are inserted into the dirty side robotic workcell. All other trays will be processed manually in the usual fashion.

On the dirty side of the CSS under the present disclosure, system 100 preferably automates the following functions: identifying the surgical instruments; unloading them from specially designed robot-ready inserts; cleaning the instruments; inspecting them for cleanliness; opening and/or closing instruments; reloading the tray inserts; and processing the inserts through an ultrasonic cleaner.

On the clean side of the CSS, the presently disclosed system preferably automates the following functions: identifying the surgical instruments; modifying a count sheet; sorting the instruments; inspecting instruments for mechanical integrity; inspecting instruments for functionality; marking instruments with barcodes or other identifying tags; pulling defective or unclean instruments; replenishing missing or defective instruments; performing instrument maintenance such as lubricating, sharpening, and demagnetizing; flipping instruments into a preferred orientation; and repacking the tray inserts.

System 100 operates with the use of robot-ready surgical tray inserts. Inserts for surgical trays are organizational tools designed to separate like instruments or hold instruments in a prescribed fashion. There are many varieties of inserts across many fields of surgery.

The present tray inserts are designed to achieve three goals. These goals include (a) ease of loading/unloading by a human, (b) ease of loading/unloading by a robotic manipulator, and (c) proper presentation for the instruments when in the washer/disinfector. Efforts to robotically automate a process are often thwarted by the difficulty in achieving consistency across the boundary from human control of a process to robotic control of a process. The use of custom tray inserts represents one potential solution to this problem in the context of the CSS.

Figure 5:
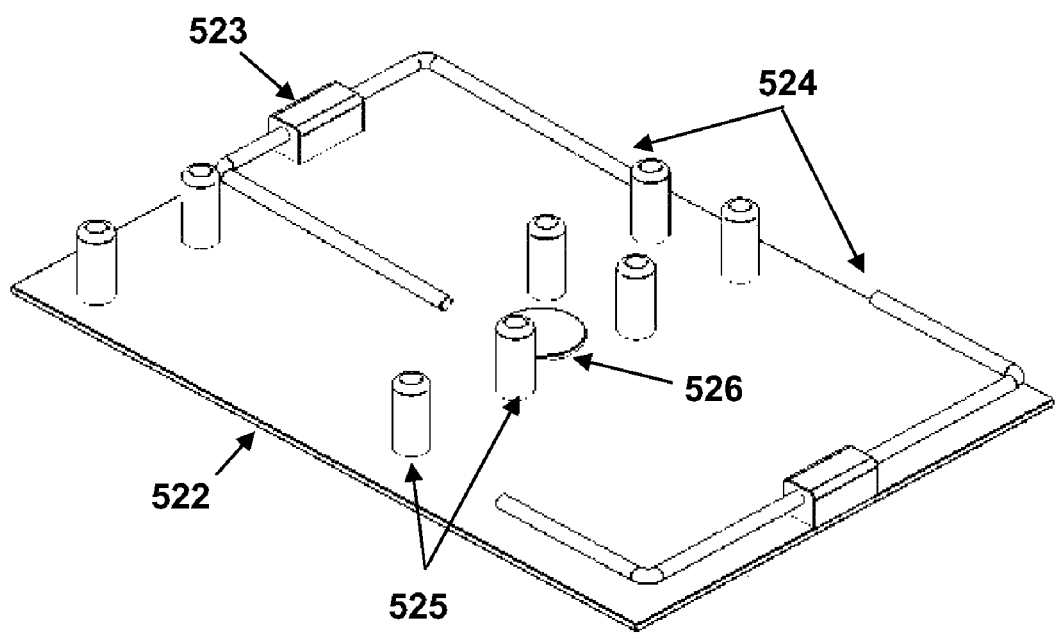
FIG. 5 shows an exemplary tray insert comprising stringers configured for use in the system of FIG. 1.
Figure 4:
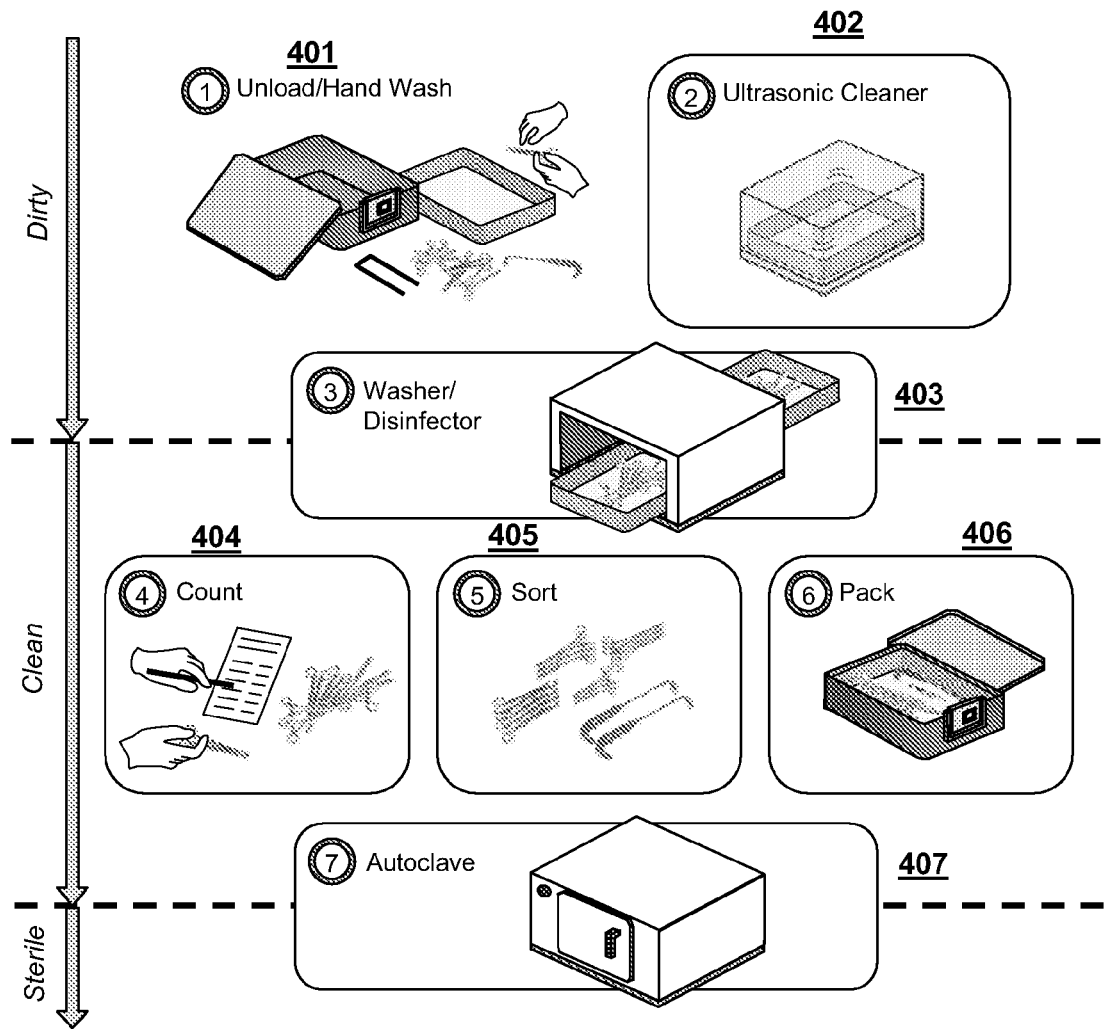
FIG. 4 shows a conventional flow process for cleaning and processing surgical equipment in an associated surgical container.

One example of an insert is shown in FIG. 5. The illustrated insert functions as an organizational tool for looped surgical instruments and comprises of a body with features including a flat plate 522, multiple stringers 524 on hinges 523, a plurality of pairs of pegs 525, and a robotic gripping point 526. The insert is designed to fit inside of standard surgical instrument trays. It is also designed to be stackable with itself and/or similar inserts that may be designed to hold other types of instruments.

Use of the tray insert in FIG. 5 is shown in the photographs of FIG. 6(A)-(E). As can be observed from the photographs, the hinged stringers are designed to hold instruments in the extreme open position. There are varied sizes of looped instruments, so a plurality of stringers are preferred. When empty of instruments, the stringers may be arranged to lie flat, and thus parallel with the tray (see FIG. 6(A)). In this position, they may be latched in place.

The pairs of pegs 525 are designed to hold instruments in the soft close position. Looped instruments of any size may fit on the pegs. The pegs may be used for homogeneous or heterogeneous stacks of instruments. A homogeneous stack refers to multiple instances of one type, while a heterogeneous stack refers to multiple instances of several types. The positions of pegs 525 on the insert are such that a maximum length instrument is permitted. Excessive length will be indicated by the instrument hanging off the insert or being obstructed by another object of the insert. The maximum length may be demarcated by an indentation in the insert or some other marking.

A preferred use of this style of insert is as follows. Instruments should be loaded onto the hinged stringers at any point prior to the washer/disinfector stage of the sterilization process. To load instruments, a stringer is pulled up into the load/unload position (FIG. 6(B)). A physical barrier or another method may be employed to hold the stringer at an approximately vertical position.

The stringer holds itself in the load/unload position, and the loops of the instruments should be placed around the lengths of the hinged stringer. Instruments are oriented on the hinged stringer (FIG. 6(C)) such that were the stringer returned to the flat position, they would point upwards. Once all the instruments are loaded, the stringer is returned to the flat position (FIG. 6(D)). This positions them ideally for the washer/disinfector.

Large looped instruments will fit onto the hinged stringers intended for smaller instruments, but with an open angle less than that corresponding to the extreme open position. Instruments should be loaded onto the largest hinged stringer they fit on. When the inserts are removed from the washer/disinfector, the instruments are unloaded for counting and sorting. To unload the instruments, the stringers are placed in the load/unload position. The instruments are removed from the stringers, and then the stringers are laid flat once again.

Figure 6:
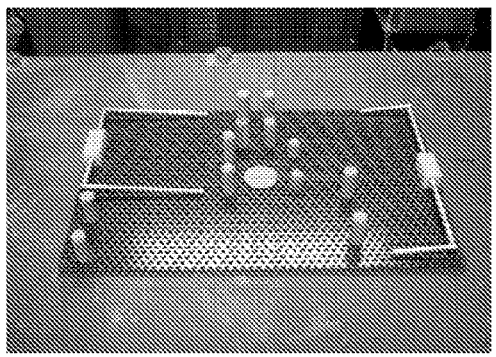
FIG. 6A-E shows examples of various stringer configurations for the insert of FIG. 5.
Figure 6:
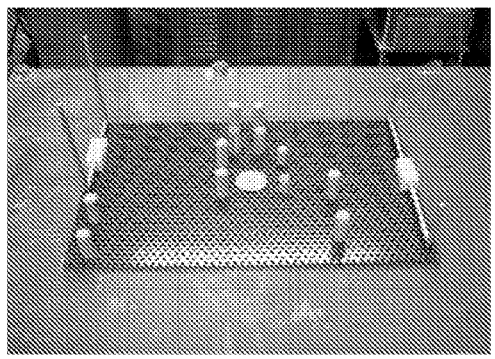
Figure 6:
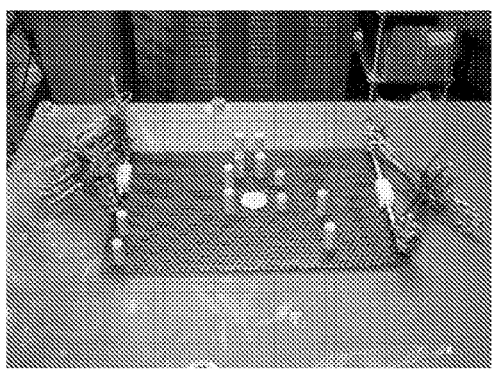
Figure 6:
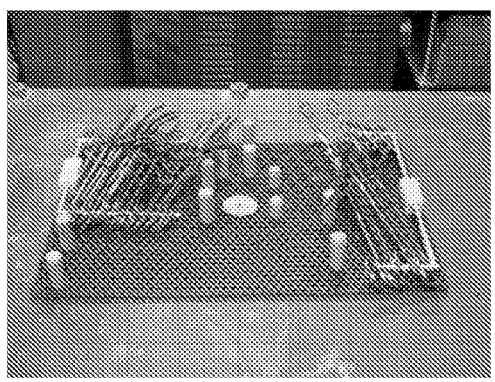
Figure 6:
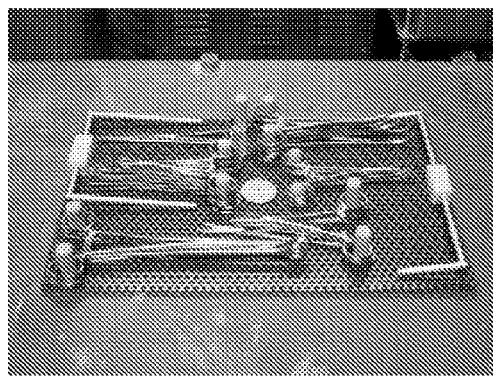

As the instruments are counted and sorted, each type of instrument and all of its instances are placed on appropriate pegs (FIG. 6(E)). When this task is completed, the insert can be placed in the tray, and is ready for sterilization and use in the OR. An insert advantageous for robotic use would have a designated gripping point 526 for the robot and have any of a variety of features allowing them to be manipulated by a robot.

The hinged stringers can also be moved from the flat position to the load/unload position by a robotic manipulator, and designed so a robot can place an appropriately opened instrument on it when in the load/unload position. Furthermore, The hinged stringer is designed so that a robotic manipulator can remove an instrument from it when in the load/unload position. The hinged stringers also can be moved from the load/unload position to the flat position by a robotic manipulator. The pairs of pegs for the insert are designed so a robot can place an appropriately opened instrument on them. The pairs of pegs are also designed so a robot can remove an appropriately placed instrument from them.

The insert may be assembled from the following groups of subcomponents:

- A single piece incorporating the tray, peg pairs, and the hinges. The stringers would be separate entities.
- A single piece incorporating the tray, peg pairs, and the lower half of the hinges. The upper half of the hinges and the stringers would be separate entities.
- A reconfigurable tray design with separate peg pairs and hinge assemblies allowing for their placement into custom positions.
- Any permissible combination of the above.

The hinges (523) may be configured to be tight around the stringer, or alternately loose, allowing the stringer to wobble. This will improve the flow of the various fluids in and around the hinged stringer during the sterilization process. The stringers may be held in the flat position by any one of the following: ball spring plunger mechanisms, cable/tool clip style snap-in, and/or magnetic attraction. The hinged stringers may also use a spring and latch design. The latch would hold the stringer in the flat position. When released, the spring would return the stringer. The methods by which the stringer is held in the flat position could also serve as a barrier to the instruments sliding off the end of the stringer when in the flat position.

The stringers may incorporate numerous variations, including adjustable width, multiple pairs of legs allowing for varied instrument size and/or multiple stacks of instruments in the soft close position, and curved legs to stabilize instruments when rotating stringer.

Figure 7:
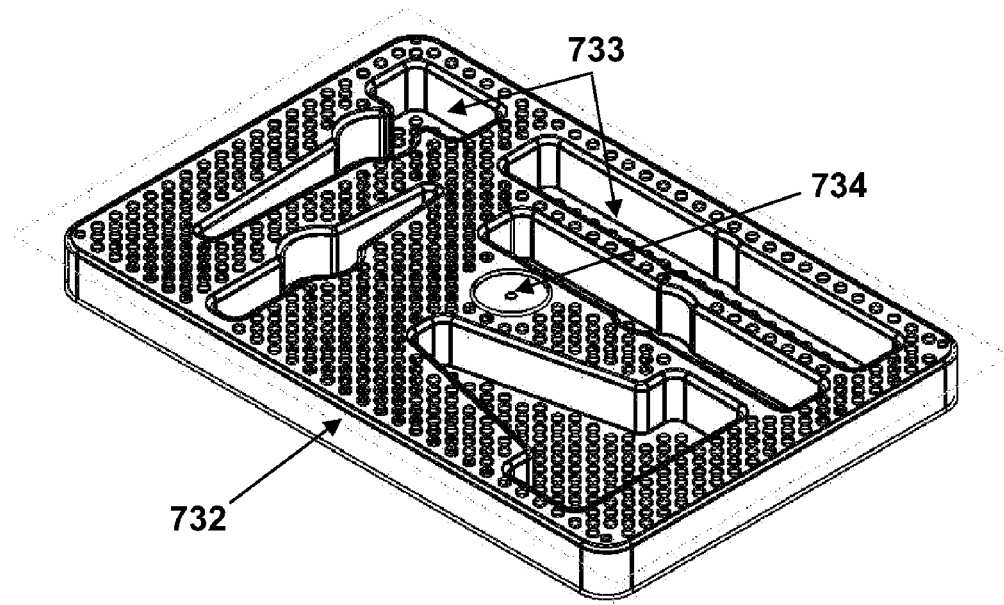
FIG. 7 illustrates another exemplary tray insert for use in the system of FIG. 1, comprising robot-ready slots.

An alternate embodiment of an insert is shown in FIG. 7. The exemplary insert functions as an organizational tool for non-looped instruments and comprises a contoured body 732 shaped with slots 733 and a robotic gripping point 734. It is designed to fit inside of standard surgical instrument trays and be stackable with itself and similar inserts which may be designed to hold other types of instruments.

The slots for the insert of FIG. 7 are varied in size and shape. Top edges of the slots are filleted to facilitate quick loading. The slots are designed to permit the size/shape of the end-effector of the robotic manipulator to reach the bottom of the slot in at least one location. When the insert is in a disorganized state, the slots are configured to have the capacity of holding a variety of instruments. In the disorganized state, an appropriate slot for a given instrument is one which the instrument will fit into while not extending above the top of the insert. When the insert is in an organized state, the slots are intended to a hold certain instrument type or group of instrument types. In this state, the instruments pertain to a prescribed slot. The prescribed type or types may be demarcated by an indented outline of the instrument or some other marking on or near the slot.

Under an exemplary process of use for the FIG. 7 insert, after use in the OR, the slotted inserts are considered to be in a disorganized state. Instruments may be placed into any appropriate slot. Once the insert reaches the CSS, the instruments are removed one by one and washed. The insert is considered to be in a disorganized state and the instruments may be placed back into any appropriate slot. This is how they will remain until they are removed from the washer disinfector.

After the washer disinfector, the instruments are counted and sorted. First they are removed from the slots. Once the insert is cleared of instruments, it is considered to be in the organized state of use, and the instruments must be returned to their prescribed slots. When every instrument is replaced in the insert, the insert is ready to be replaced into the surgical instrument tray, which may then be placed in a container for sterilization.

Figure 17:
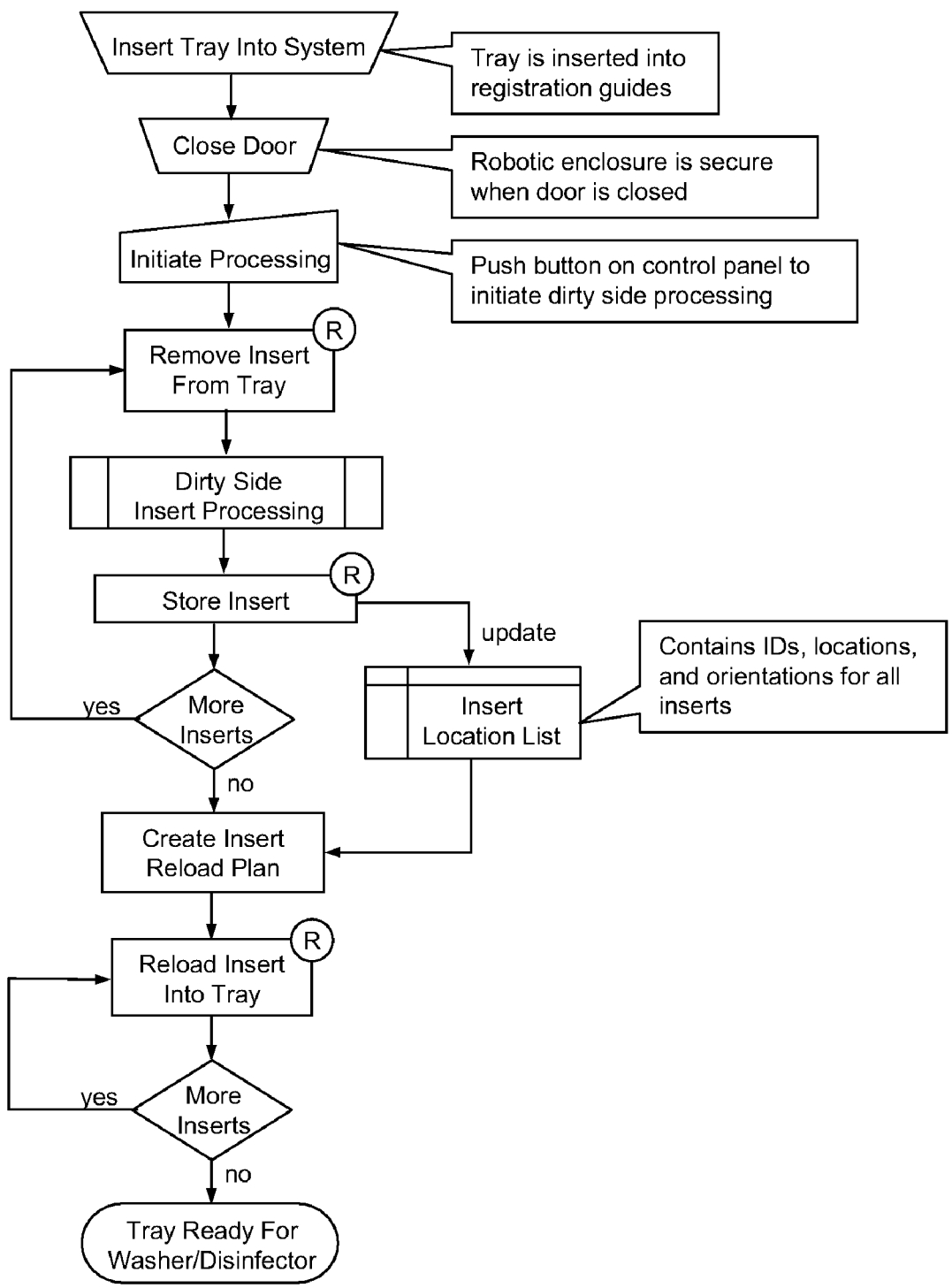
FIG. 17 is an exemplary flowchart for sub-processes related to dirty side processing.

An exemplary dirty side processing is detailed in the flowchart in FIG. 17, the configuration of which is illustrated in FIG. 2A. Trays are inserted for processing into the robotic workcell's input slot 206. Registration guides ensure that these trays are located in a fixed, repeatable location within the robot's envelope of operation. After inserting the tray, the system's door 104 should be closed to secure the robot for safe operation. The automated tray processing is then initiated by pressing a button or choosing an option from an electronic display.

Figure 18:
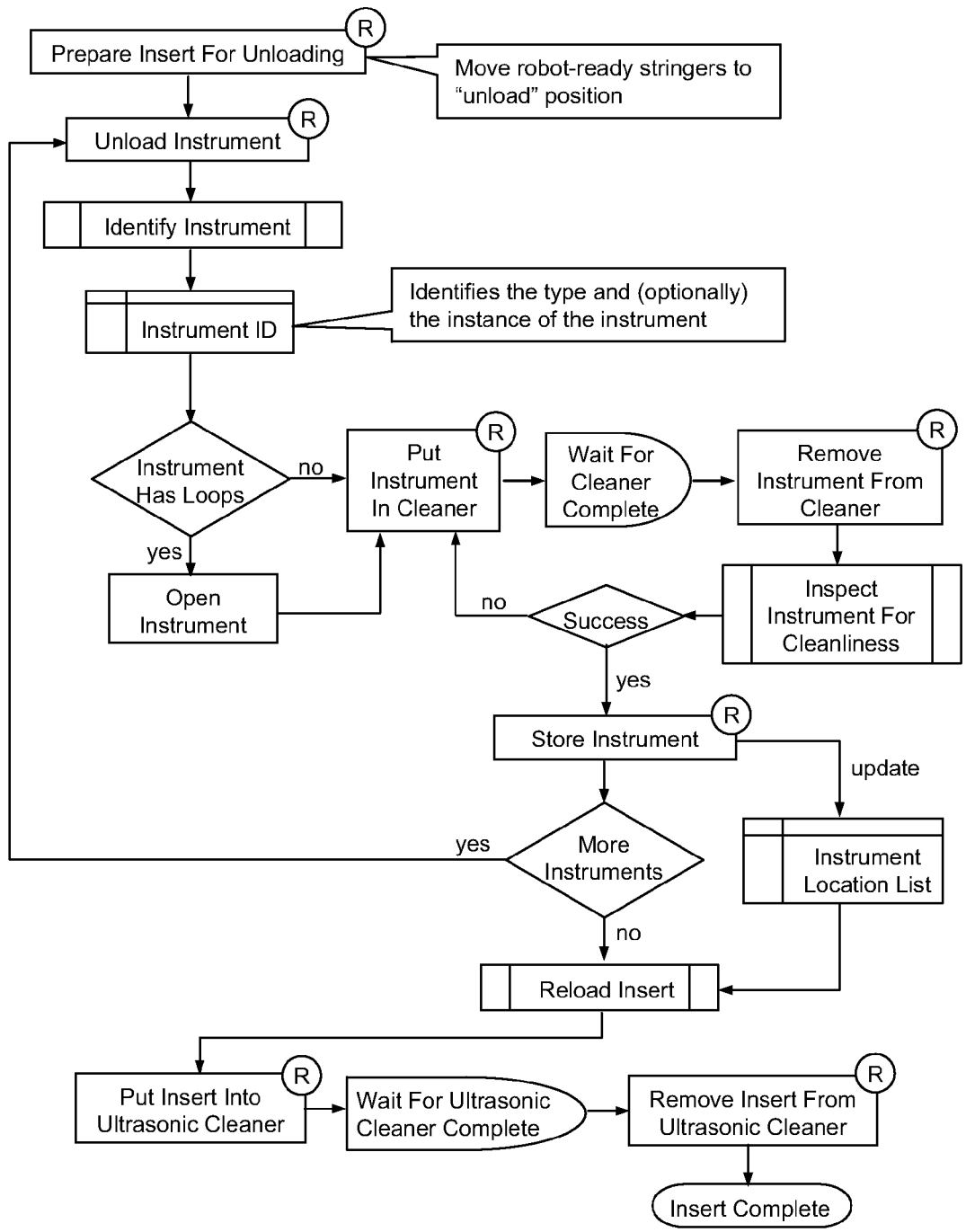
FIG. 18 is an exemplary flowchart for sub-processes related to dirty side insert processing.

The robot will then remove the first specially designed insert from the tray and begin processing it, as shown in the flowchart in FIG. 18. The insert is made ready for unloading as described above. This involves raising the robot-ready stringers to the unload position (FIG. 6(C)) if required. A detailed description of the instrument unloading process is included below.

As the instruments are unloaded, they are identified. A detailed description of this process is included below. An instrument identification includes the type of the instrument, such as "Kelly Clamp" or "Richardson Retractor". This type is used at various stages of the downstream processing. The identification can also include a code distinguishing each instance of this instrument from the others. This information can be used downstream to track maintenance schedules and usage statistics.

An instrument opener is used to ensure that looped instruments are in the soft open position at this point. A detailed description of the instrument opener is provided below. Soft opening allows the robotic gripper to securely grasp the instrument as it is moved from place to place. An instrument in the soft open position can be grasped just above the hinge so that the two independent hinged sides don't move relative to one and other while the robot is in motion.

Turning to FIG. 18, the instrument is then inserted into a robot-ready instrument cleaner for scrubbing and washing. When this process is concluded, the robot retrieves the cleaned instrument and inspects it for cleanliness. This process is described in detail below. If the instrument is found to be unclean, it can be run through the washer again. The system can be configured to repeat this wash/inspect loop as required for a set number of iterations before rejecting the instrument for manual processing. When the instrument has been successfully cleaned, the robot stores in the instrument temporary storage area (208). This area should be sufficiently sized to accommodate all the instruments in one tray insert. As each instrument is stored, its location and orientation are stored in memory so that the robot can later retrieve it.

Figure 21:
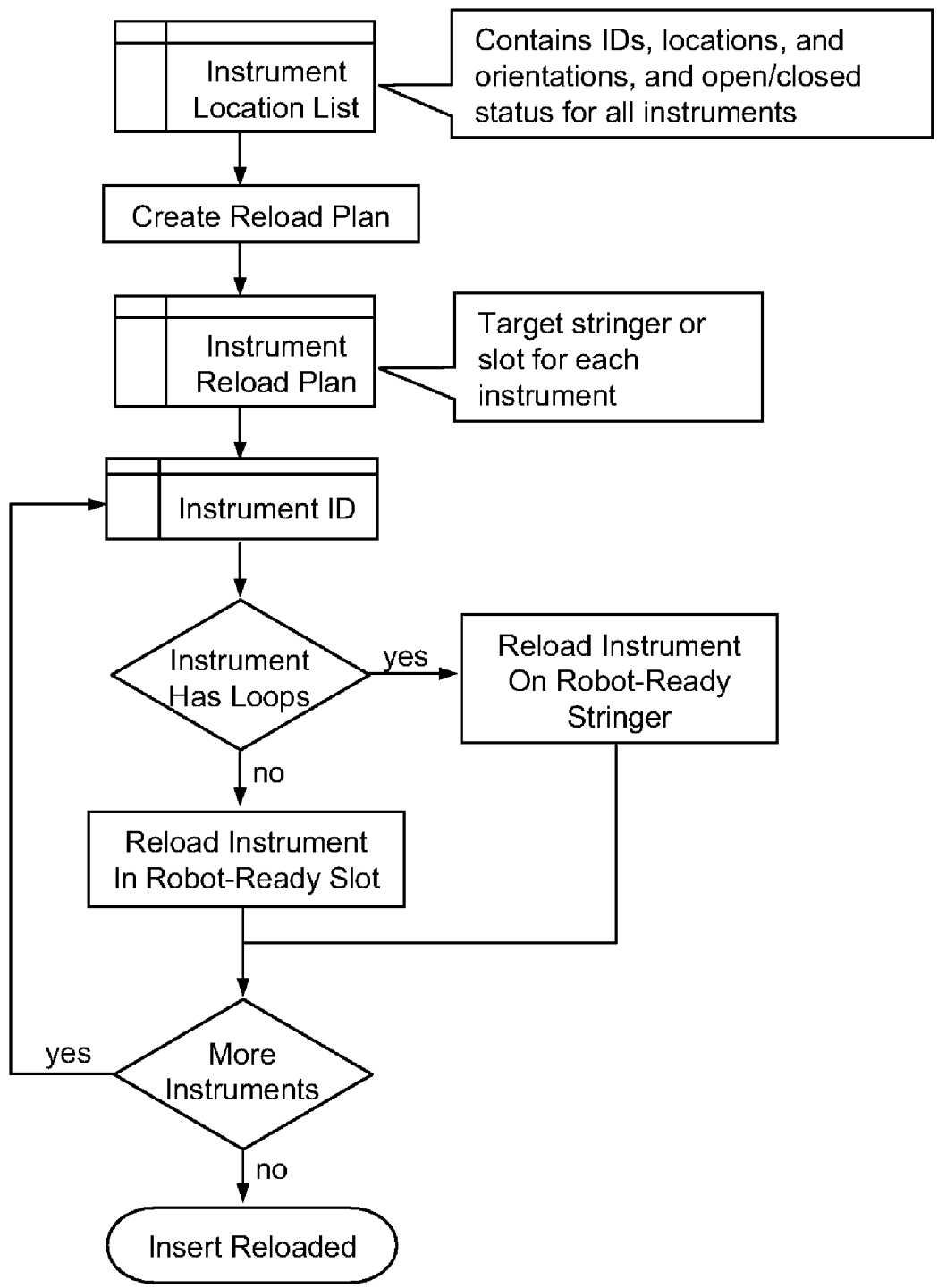
FIG. 21 is an exemplary flowchart for sub-processes related to insert reloading.

Once all of the instruments have been cleaned, the insert is reloaded as described in the flowchart of FIG. 21. This process is substantially the reverse of the unloading process descried in detail below. The control software develops a reload plan specifying the locations and order of each instrument in the insert. Reload plans under the preferred embodiment can reflect hospital preferences, desired instrument orientations, and insert capabilities. For example, looped instruments can be reloaded back onto the robot-ready stringers or into robot-ready slots. The former case is preferred for the insert reload on the dirty side as it best presents the instruments for cleaning in the washer/disinfector.

The reloaded insert is then placed into an ultrasonic cleaner and/or enzymatic solution bath. This process may take some time so the robot is free to work on the next insert at this point. When all inserts have been processed and reloaded into the tray, dirty side processing is complete. The tray may then be removed from the robotic workcell and put in the washer/disinfector.

Unloading/Reloading Robot-Ready Stringers

After removing the insert(s) the robot 102 will removes instruments from the robot-ready stringer. The control software commands the robotic arm to move to a fixed location just above a left prong of the upright stringer. Since the location of the insert within the workcell is known, and the dimensions of the insert are known, this location is deterministic. The control software will then command the arm to move in a straight line directly above the left prong until either the loop of an instrument or the bottom of the insert is encountered. This event can be detected with a mechanical "bump" switch on the robot's end-effector, a proximity sensor, using force feedback from the robot's motors, or other means. If distance traveled is equal to the length of the prong, no looped instrument was found on the stringer. Otherwise, the presence of an instrument will be detected and prepared to be grasped, where the robot's motion may be reversed, pulling the instrument off the stringer. The robot can grasp the instrument by means of an electromagnet force, a suction device, a mechanical grasper, or other means. The robot can then lay the instrument down and repeat the process until the stringer is empty. Later in the process these robot-ready stringers will be reloaded. This process is the same as above, only in reverse.

Unloading/Reloading Robot-Ready Slots

Instruments without loops are stored in specially shaped slots on the insert. These slots are designed with a cutout so that the robot's gripper can descend into the slot to pick up (or drop off) instruments. This process is substantially similar to that described for robot-ready stringers above. The control software commands the arm to a point above the slot and then along a straight line directly down into the slot. As before, this motion continues until either an instrument or the bottom of the slot is detected. If the distance traveled corresponds to the slot's depth, no instrument was found. Otherwise, the instrument is grasped and the robot reverses its motion to pull the instrument out of the slot. Later in the process these robot-ready slots will be reloaded. This process is the same as above, only in reverse.

Identifying Instruments

Figure 19:
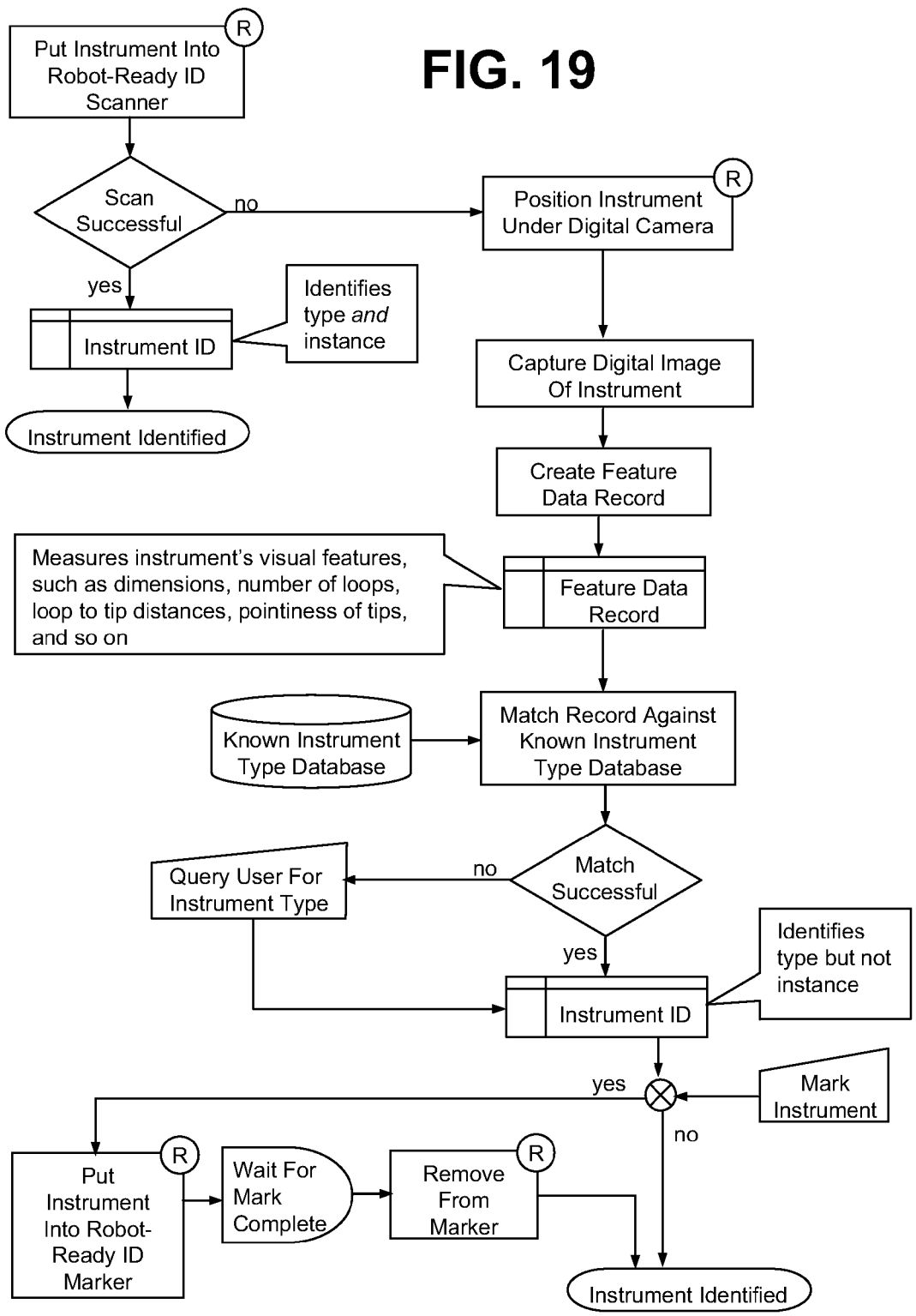
FIG. 19 is an exemplary flowchart for sub-processes related to identifying instruments.

The instrument identification process is shown in FIG. 19, where the type of instrument and/or the unique instance of the instrument can be identified. There are several identification alternatives. One is through an identifying mark on the instrument such as a bar code or RFID tag. Another technique utilizes machine vision technology to identify the type of the instrument.

When identifying instruments via a barcode, the robot performs the functions of a human scanning the code. There are alternatives design options. A standard barcode scanner can be attached to the robot's end effector. In this scenario the robot will move the scanner over the instrument to scan it. In another scenario, the robot inserts the instrument into a stationary version of a standard barcode scanner. In either case the robot is programmed with the optimal scanning distance, orientation, and rate so as to improve the successful scan rate.

Instrument identification can alternately be accomplished using a number of commercially available solutions such as InfoDots™ by Unique Micro Design, Censitrac™ by Censis Technologies, Inc., and Abacus. The identification under the present disclosure may utilize any of these solutions and/or any scanner-based barcode or RFID solution. Since the system's robotic arm may programmed to mimic a human arm with a handheld scanner, any such system would be suitable. Additionally, physical instrument identifications can accomplished by marking instruments using a commercially available system such as the Synrad™ Co2 Laser Marking System.

Identifying Instruments: Machine Vision

Instrument identification via machine vision relies on well-known algorithms known in the art. Commercially available systems include such products as supplied by Cognex™ and MathWorks™, and can be suitably configured to perform these functions. In general, the process includes the following steps:

(1) Acquire a single frame of image data from a digital camera;
(2) Filter out unwanted portions of the image. This includes static, fixed areas as well dynamic areas such as the pixels obscured by the robotic arm as it moves within the vision system's field-of-view;
(3) Separate pixels in the foreground of the image from those in the known, fixed background;
(4) Collect remaining foreground pixels into contiguous regions called blobs. If these regions are segregated properly, each blob will correspond to one object;
(5) Compute a vector of defining characteristics from each blob. These characteristics include length, breadth, and mass. Also compute each blob's center of gravity and orientation; and
(6) Compare the characteristic vector for each blob against a training database of characteristic vectors for all known objects. If the measured characteristic vector is statistically close to the training vector, identify the object thusly.

Machine vision is preferably configured to only identify the presence and type of instrument in question and not the individual instance. The process described above may need to be repeated for other vantage points such as the instrument's side. Some instruments differ only in the amount of curvature at the tip, which is difficult to measure from a top down image.

In an optional step, after the instrument has been identified by machine vision, the robot can insert the instrument into a specially designed barcode or RFID marking device. This device will etch or otherwise mark the instrument with a unique identification code so that it can be scanned on subsequent trips through the system.

Opening Instruments

Figure 10:
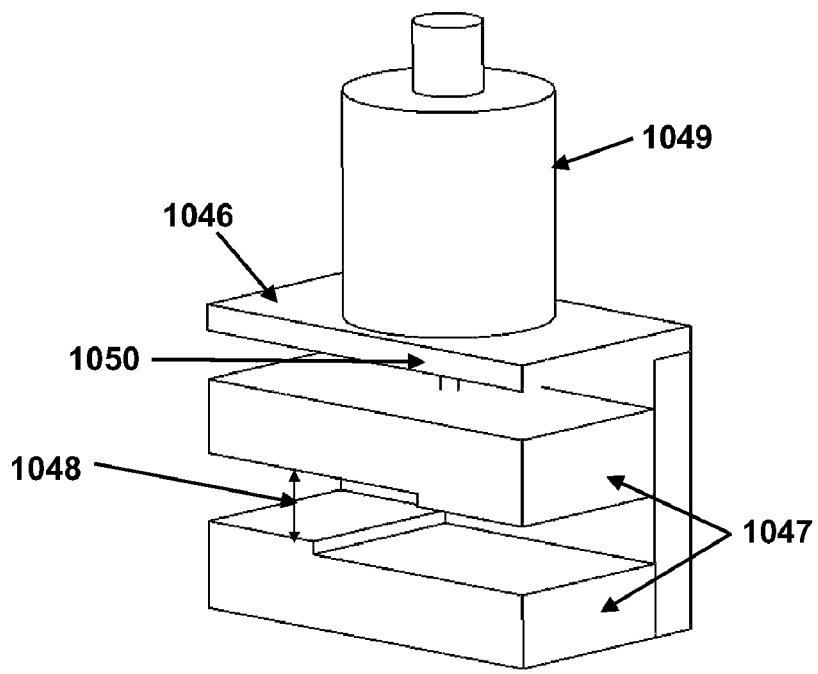
FIG. 10 illustrates a perspective view of an exemplary instrument opener that the robot may use to open looped instruments.
Figure 11:
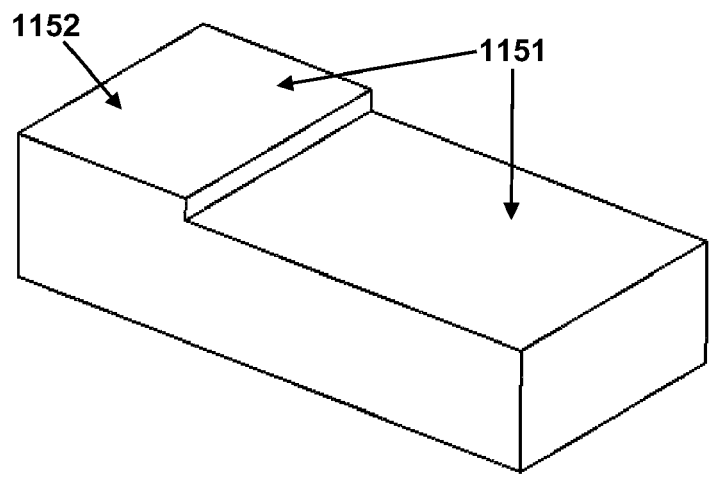
FIG. 11 shows a contoured face detail of a portion of instrument opener illustrated in FIG. 11.
Figure 12:
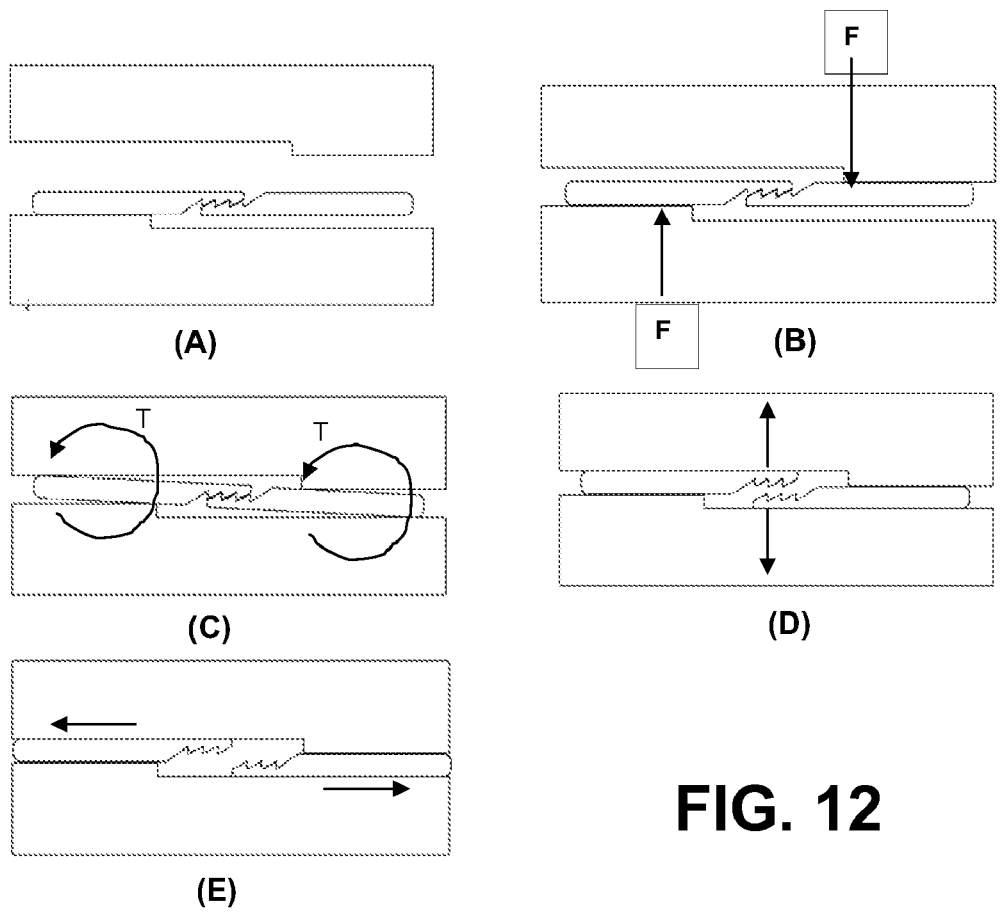
FIG. 12A-E illustrate an exemplary instrument opening process using instrument opener shown in FIGS. 10-11.

The instrument opener is a device designed to open surgical instruments which have a ratchet lock mechanism. The instrument opener functions by forcibly pushing the two ratchets of the instrument apart. An exemplary embodiment of a preferred instrument opener is shown in FIGS. 10-12. Turning to FIG. 10, the instrument opener comprises a body 1046, two jaws 1047, having contoured faces 1048, an actuator 1049, and a drive train 1050. One jaw of the instrument opener may be stationary, while at least one jaw is connected to the actuator through the drivetrain. The sweep of the jaws refers to the three dimensional volume through which the movable jaw(s) close. The contoured faces 1048 are opposed to one another. As can be seen in FIG. 11 the contoured faces have two levels 1151, with the raised level 1152, preferably having less surface area than the lower level. The faces are arranged rotationally symmetric about an axis parallel to the z axis of FIG. 10. Once activated, the actuator forces the contoured faces 1048 towards one another.

Turning to FIG. 12, subparts (A)-(E) illustrate an exemplary opening process. Instruments to be opened are placed or held such that finger rings are between the contoured faces of the jaws (FIG. 12(A)). As the jaws close, the raised level of the faces will contact the finger rings (FIG. 12(B)). As the jaws continue to close, a torque resulting from the forces ("F") applied by the raised level 1152 of the jaws will rotate the instrument about an axis roughly corresponding to the length of the instrument. The instrument will rotate ("T") until the outer edges of the finger rings contact the lower level of the corresponding jaw face (FIG. 12(C)). As the jaws continue to close, parallel torques are applied to each finger ring (FIG. 12(C)). The shafts of the instrument deflect in opposite directions, disengaging the teeth of the ratchet (FIG. 12(D)). The spring force stored in the shaft resultant from the force required to close is no longer impeded by the ratchet, and spreads the finger rings apart (FIG. 12(E)).

In addition, the following variations are also possible under alternate exemplary embodiments of the instrument opener.

The opener body may include a surface coincident with the raised level of the lower jaw which the instrument to be opened may be set upon.

The opener body may include walls or some other obstruction to physically limit the distance the finger rings may separate resulting from the spring force.

The actuator may be a solenoid directly driving the upper jaw.

The actuator may be a servo motor connected to a linkage mechanism.

Closing Instruments

Figure 9:
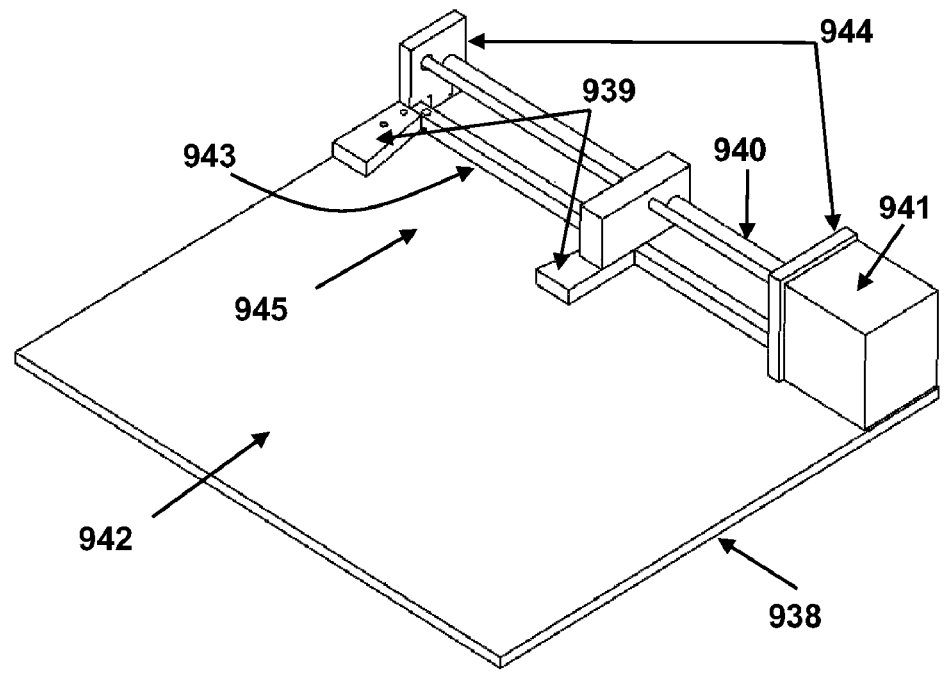
FIG. 9 illustrates a perspective view of an exemplary instrument closer that the robot may use to close looped instruments.

The instrument closer (an exemplary embodiment is illustrated in FIG. 9) is a device designed to automatically close hinged surgical instruments to a prescribed distance. The task is accomplished by forcing together the finger rings of applicable instruments.

The exemplary device in FIG. 9 is a device for closing ratchet lock instruments, and comprises a body 938, two jaws 939, a drivetrain 940, and an actuator 941. The main aspects of the body include a surface 942, a backstop 943, and mounts for the actuator and drivetrain 944. One jaw may be stationary, while at least one jaw is connected to the actuator through the drivetrain. The sweep of the jaw(s) refers to the area of the surface which may be covered by the jaws at any point of their movement 945. The sweep of the jaw(s) should correlate to the shape of the backstop.

Instruments to be closed are placed on the surface with both finger rings in between the jaws, and within the sweep of the jaws. The device closes the instrument by lessening the distance between the two jaws. The geometry of the body and jaws 939, combined with the pressure from the jaws, ensures the stability of the instrument while closing.

The instrument closer can close a device to a completely closed position, or alternately to any level of partial closure. If a soft close is required, the device will go to a set distance based on the size of the instrument and the desired distance between finger rings. If it is desired to have a particular number of teeth engaged, the device will close to the requisite distance dependent on the instrument size and prescribed number of teeth.

In addition to the above, the following variations are envisioned for the instrument closer.

The device may use a stepper motor and prescribe a certain number of steps depending on the desired distance to prescribed closing.

The device may use a servo motor coupled with a controller using an optical encoder to determine distance closed.

The device may use a microphone to listen for the number of clicks generated by the engagement of the teeth. The microphone may be piezoelectric and mounted to one of the jaws, or may alternately be a contact microphone and mounted to one of the jaws.

The device may have a means of measuring the force necessary to close the instrument, which may include (1) measuring the current required to maintain a servo at a prescribed speed, and/or (2) force sensors attached to the jaws.

Inspecting Instruments For Cleanliness

Figure 20:
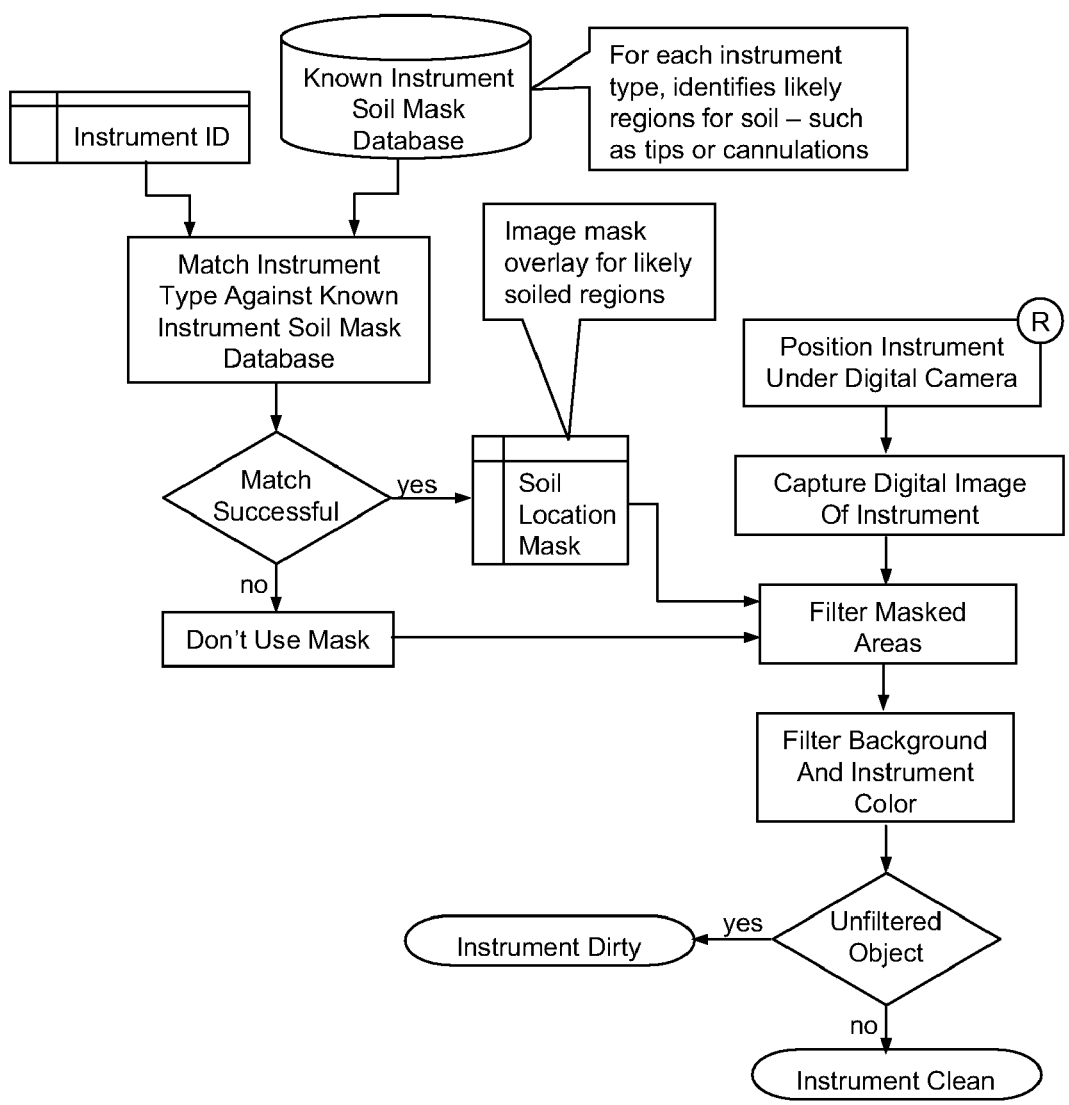
FIG. 20 is an exemplary flowchart for sub-processes related to inspection of instruments for cleanliness.

As shown in FIG. 20, machine vision algorithms can be used to inspect instruments for residual contamination by bodily fluids/tissue debris. Commercially available systems such as those offered by Cognex™ and MathWorks™ can be configured to perform these functions. For each instrument type, an image mask identifying likely regions for contamination is created. These regions may include tips, hinge boxes, teeth, and cannulations. In a process similar to the one described in "Identifying Instruments: Machine Vision" above, the background is removed from these regions of the image. If a significant number of pixels remain unfiltered, contamination may be present. Other inspection modalities such as special fluorescent lighting or chemo-sensing may be used to detect residual contamination ("bioburden") on the instruments.

Clean Side Processing

Figure 22:
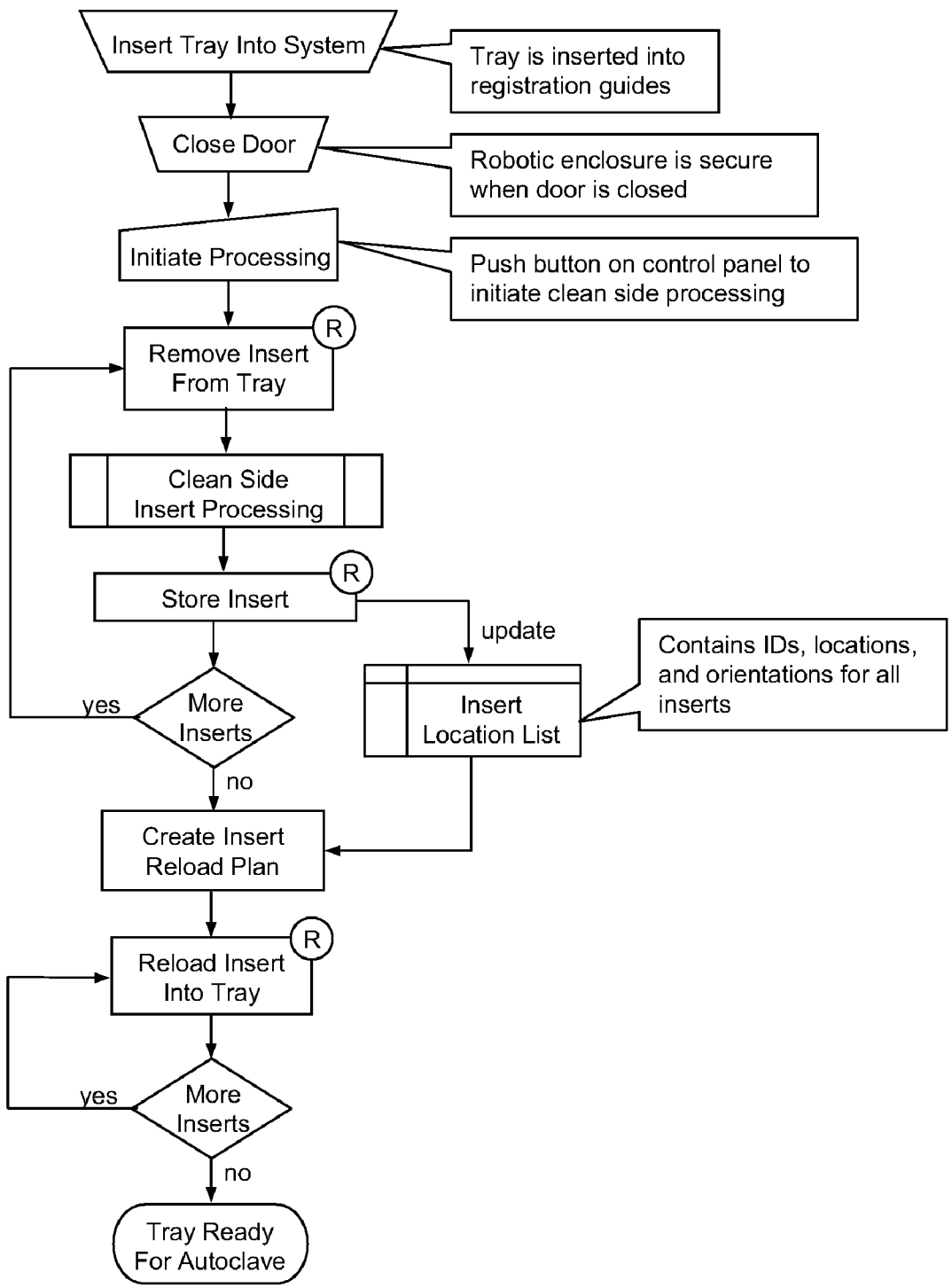
FIG. 22 is an exemplary flowchart for sub-processes related to clean side processing.
Figure 23:
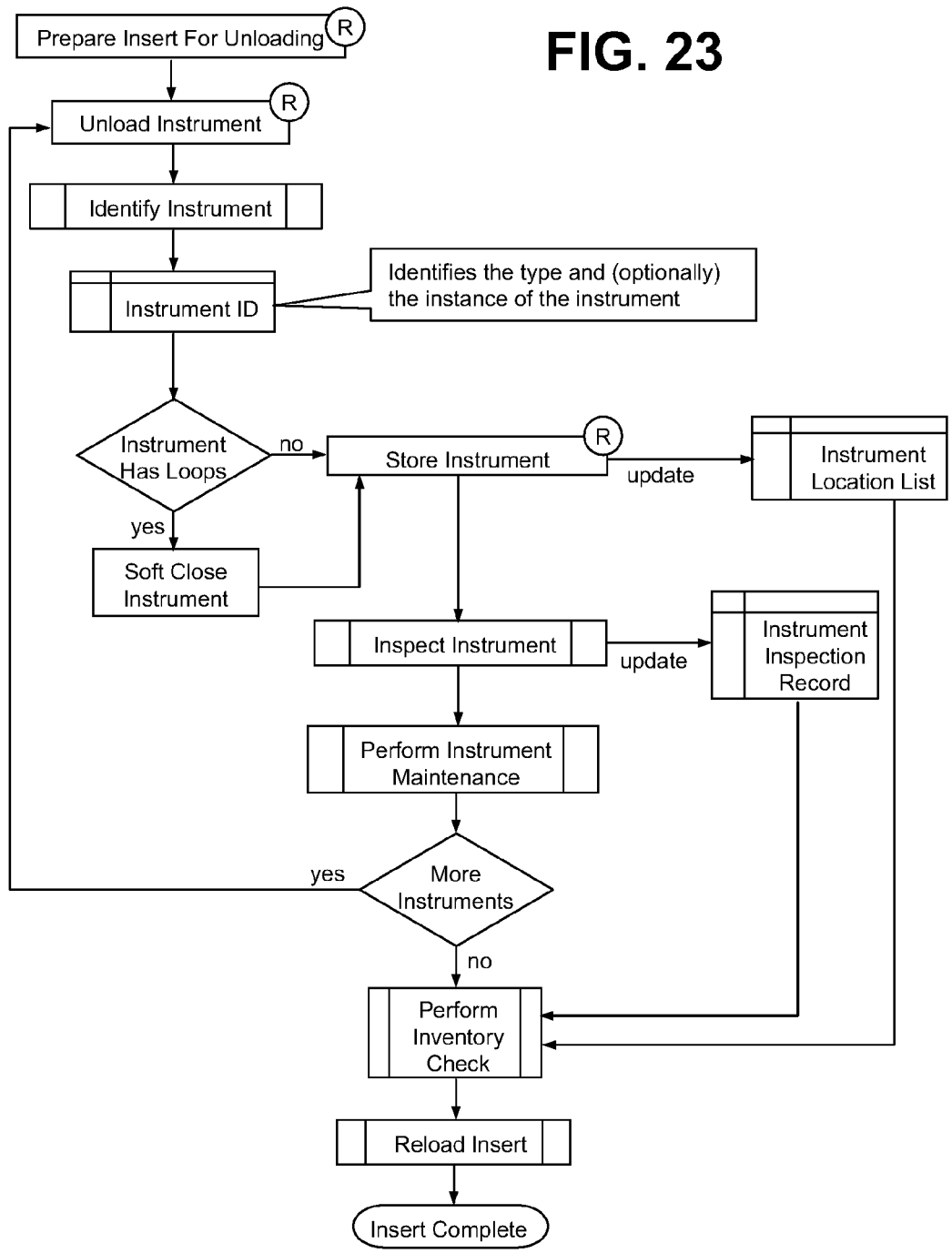
FIG. 23 is an exemplary flowchart for sub-processes related to clean side insert processing.

Clean side processing is detailed in the flowchart in FIG. 22. The clean side configuration relates to the system shown in FIG. 2B. Trays coming out of the washer/disinfector are inserted into the robotic workcell and clean side processing is initiated. The basic functions on the clean side are substantially identical to those on the dirty side and are documented above. In FIG. 23, it may be seen that the processes differ after the "Store Instrument" step.

Figure 24:
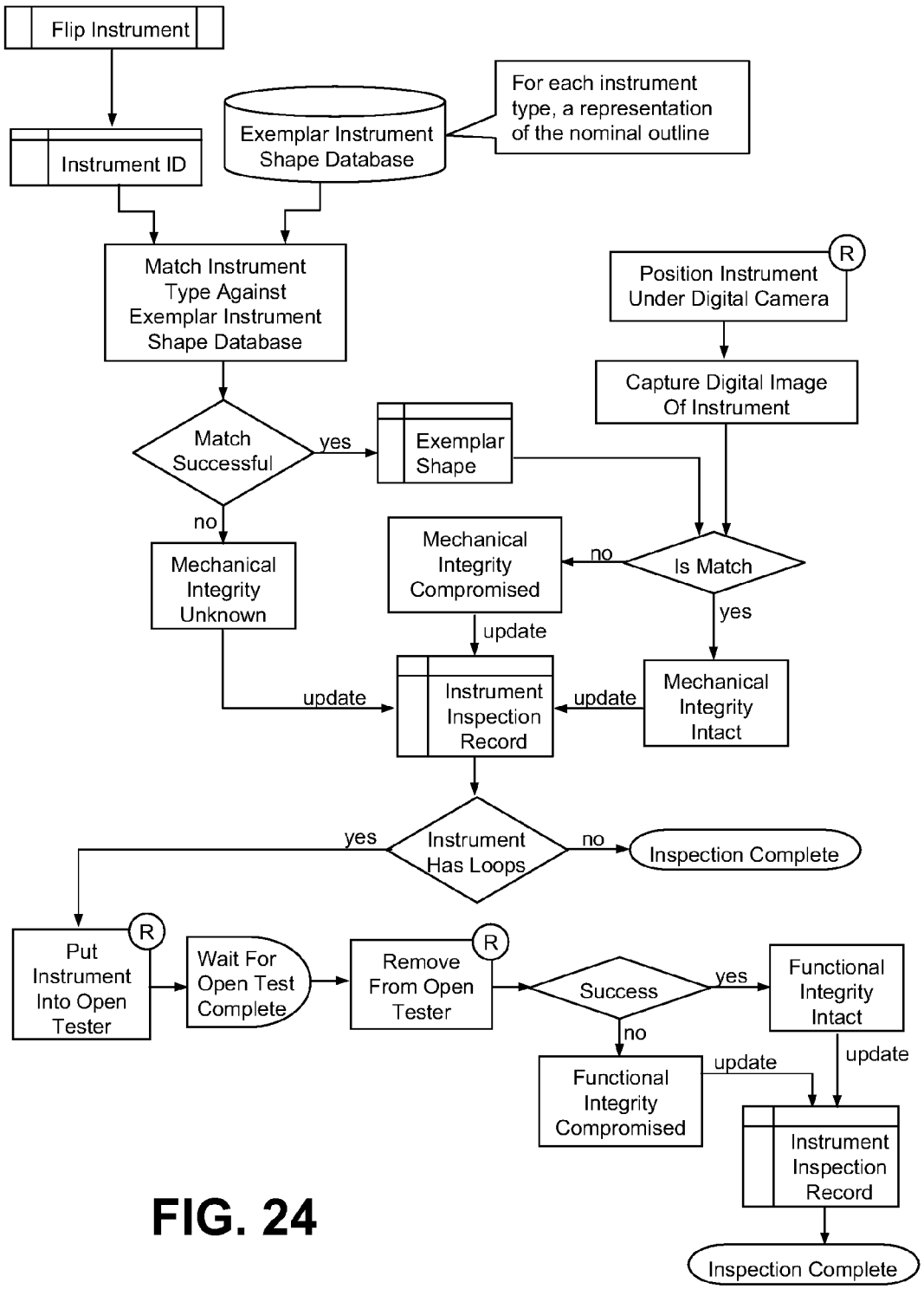
FIG. 24 is an exemplary flowchart for sub-processes related to instrument inspection.

Instruments are inspected on the clean side in a process detailed in FIG. 24. The first step is to "flip" the instrument if required. This ensures that the instrument is lying with its preferred side up. For example, some instruments have curved tips and the preferred orientation might have those curved tips facing up. A detailed description of the instrument flipping process is included below.

The instrument is checked for mechanical integrity by comparing an image of the instrument to an exemplar template shape for the instrument. Exemplar shapes for each instrument type, such as Hopkins Clamp, are defined in advance of system usage and define the proper outline for a canonical instrument of each type. The image processing required for this step is identical to that described in "Identifying Instruments: Machine Vision" above. Mechanical integrity means that no piece of the instrument is missing or deformed.

Looped instruments can become stiff and difficult to open and close over time. This can be caused by forceful use, dropping the instrument, accidental impact with another object, or gradual wear on the hinge over time. If an instrument is difficult or impossible to open, its functional integrity is said to be compromised. Instruments are tested for functional integrity using the instrument closer shown in FIG. 9 and described in detail above. The closer can measure the force required to close the instrument. If this force exceeds a configurable threshold, the instrument's functional integrity is compromised.

Figure 26:
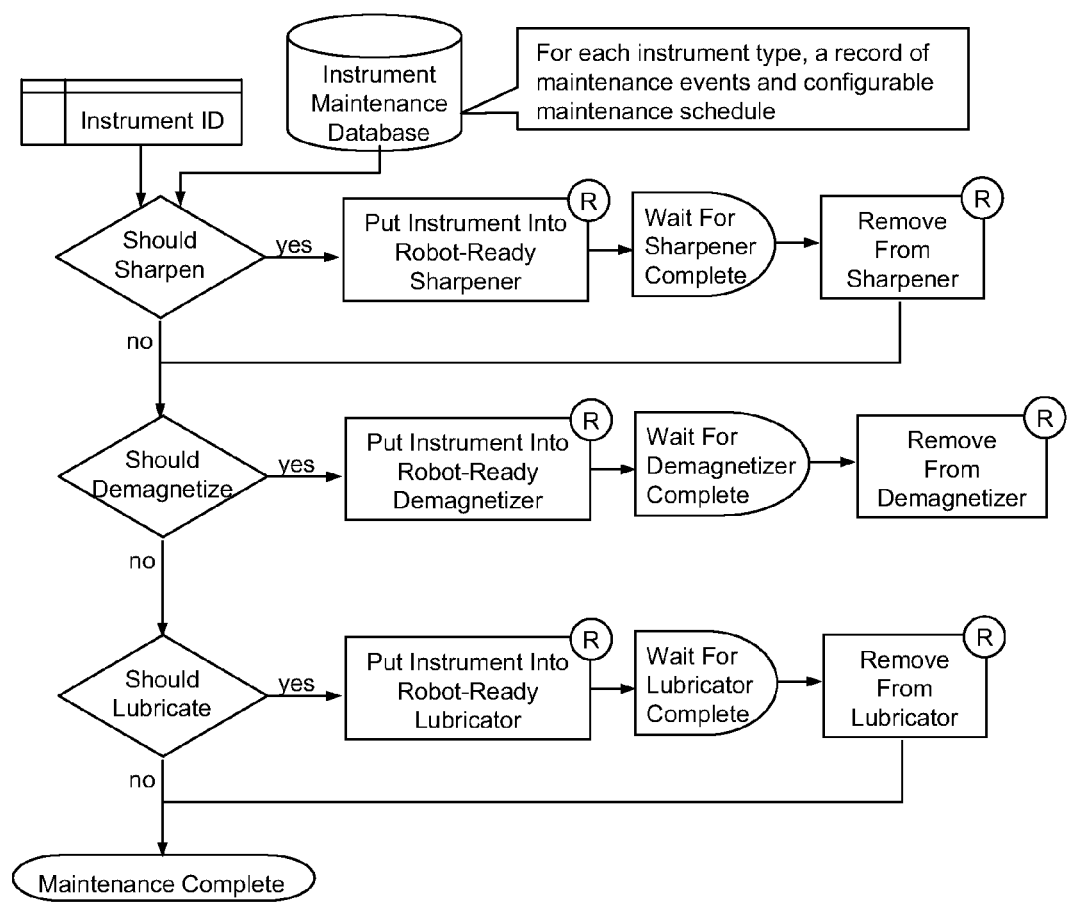
FIG. 26 is an exemplary flowchart for sub-processes related to instrument maintenance.

After inspection, the instrument goes through the routine maintenance functions shown the FIG. 26. If the instrument identification includes a code distinguishing the instrument instance, maintenance is based on previous maintenance history and the number of times the instrument has been used. Otherwise, maintenance can be configured to occur each time an instrument is processed or at a random sampling rate. For each maintenance function shown (e.g., sharpening, demagnetizing, and lubricating) the design calls for the use of a commercially available device, modified as little as possible, so as to allow the robot to use it. For example, a commercially available sharpener is used, but modified as needed to allow the robot to insert and remove the instrument as a human would. This modification turns devices into robot-ready accessories.

Figure 27:
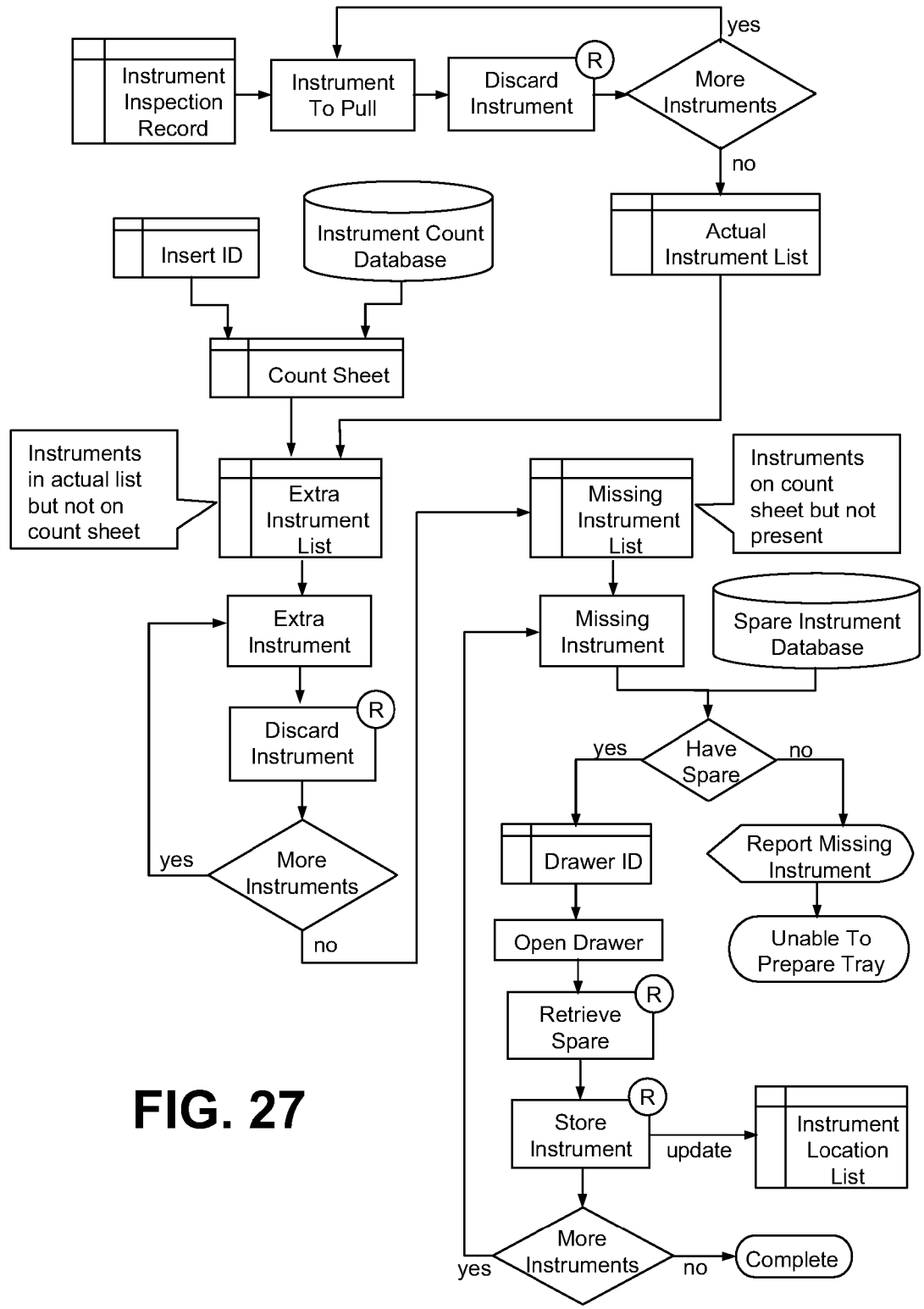
FIG. 27 is an exemplary flowchart for sub-processes related to performing inventory check.

Once all instruments have been unloaded, an inventory check is performed as shown in FIG. 27. The first step is to discard any instrument that failed one of the inspection steps. This results in the actual instrument list which is then compared to the count sheet. Any instruments in the actual list, but not on the count sheet are extra and are discarded. This can occur if the instruments we not packed in the proper containers in the OR or if the count sheet specification was changed by management. Instruments on the count sheet, but not in the actual instrument list are missing and must be replenished. A database of instrument spares indicates if the robot-ready storage cabinet (described in detail below) contains an appropriate spare. If no such spare exists, the operator is notified.

After the inventory check, the insert is reloaded. As described above, the reload plan developed here may use the robot-ready stringers or the pins on the insert. This is a matter of hospital preference. When all inserts have been processed and reloaded into the tray, clean side processing is complete. The tray may then be removed from the robotic workcell and put in a container to go in the autoclave.

Flipping Instruments

Figure 25:
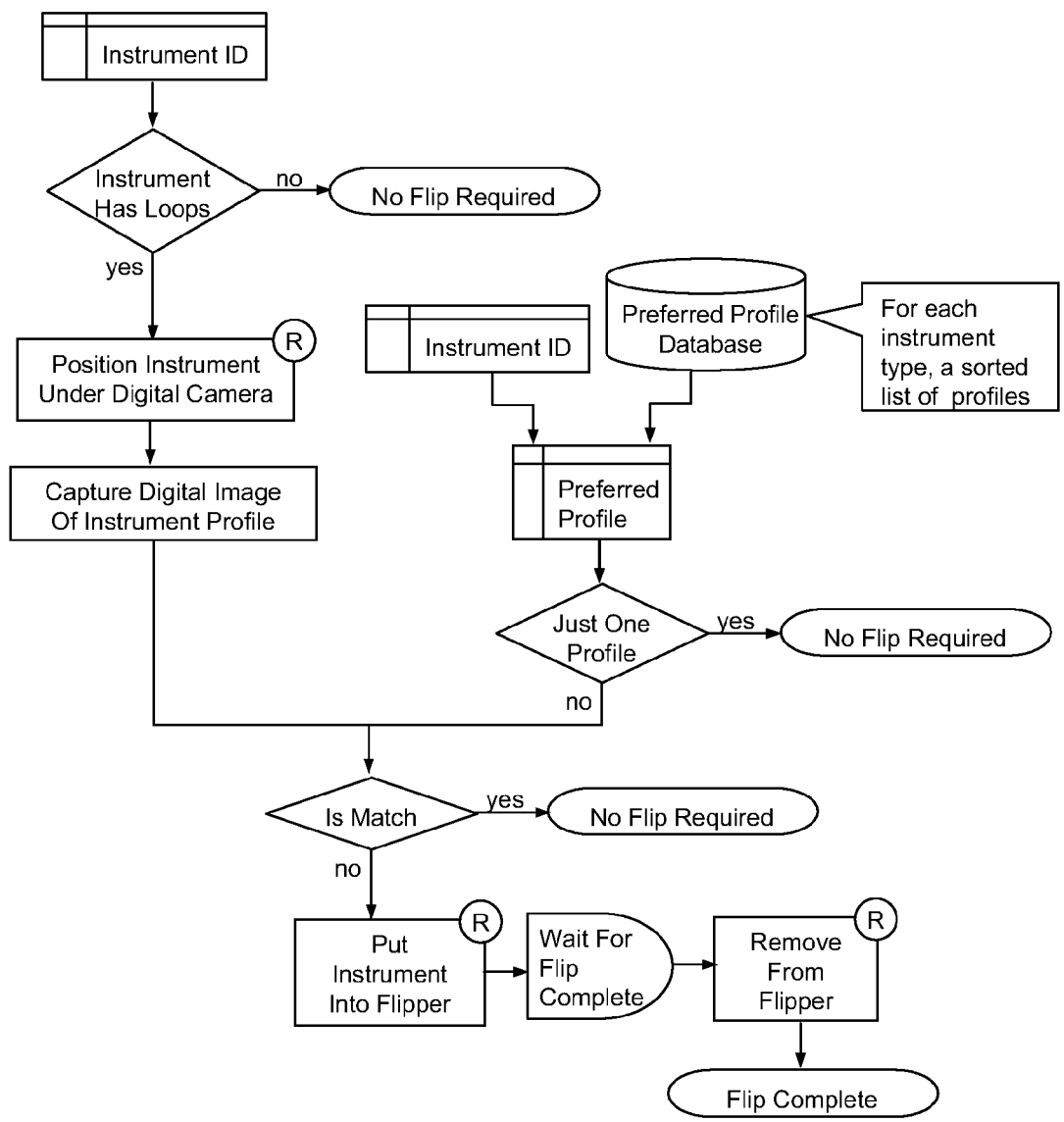
FIG. 25 is an exemplary flowchart for sub-processes related to instrument flipping.

An exemplary process for flipping an instrument is shown in FIG. 25. A database of preferred profiles is maintained for each instrument type. This is preferably a sorted list of valid orientations for the instrument. The first profile in the list is a desired orientation. These preferred profiles are equivalent to the exemplar shapes discussed in regard to mechanical integrity inspection above. Using the same process, a digital image of the instrument is taken and compared to the preferred profile. If more than one profile is known for the instrument and the image taken of the instrument does not match the preferred profile, the instrument is flipped.

Figure 13:
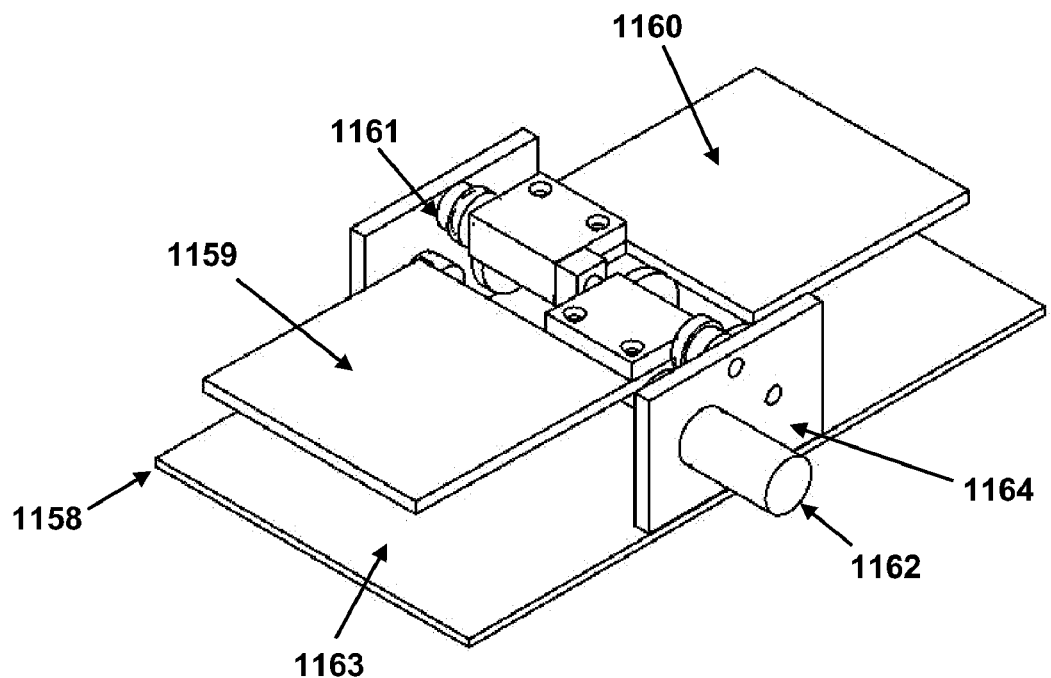
FIG. 13 is a perspective view of an exemplary instrument flipper used by a robot to flip or turn over instruments.
Figure 14:
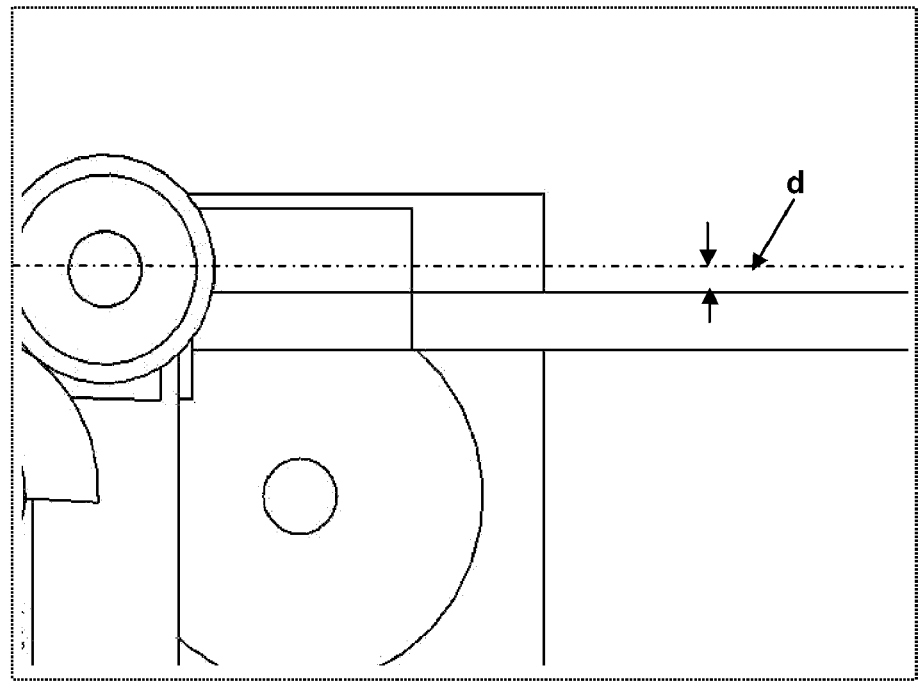
FIG. 14 is a detail view of the instrument flipper of FIG. 13.

An exemplary instrument flipper is illustrated in FIGS. 13 and 14. The flipper is a device designed to securely grasp and flip surgical instruments. A preferred embodiment of the instrument flipper consists of a body 1158, two plates: first plate 1159 and second plate 1160, a drivetrain 1161 and an actuator 1162. The main components of the body include base 1163 and mounting blocks 1164 for the actuator and drivetrain. Each plate is fixed to one of two concentric axles of the drivetrain. The plates are radially offset from the axles by a distance d (see FIG. 14). In the resting state, the plates are parallel with the base. The plates have a soft rubber surface which help for securing the instrument as well as allowing variation of instrument thickness.

The instrument to be flipped is placed on plate with its finger rings pointing towards the axle. The drivetrain 1161 transmits power to the plates in a prescribed sequence and direction. First, second plate 1160 rotates 180° to meet with first plate 1159. The instrument is secured by the pressure from the soft rubber material (not shown) of both plates. Second, the both plates are rotated simultaneously 180° in the same direction, such that second plate 1160 is in it resting state. At this stage, the instrument has been flipped. Finally, first plate 1159 rotates 180° back to its resting state revealing the flipped instrument now resting on second plate 1160. This completes the flipping process and renders the device prepared for the next flipping.

Robot-Ready Storage Cabinet

Figure 8:
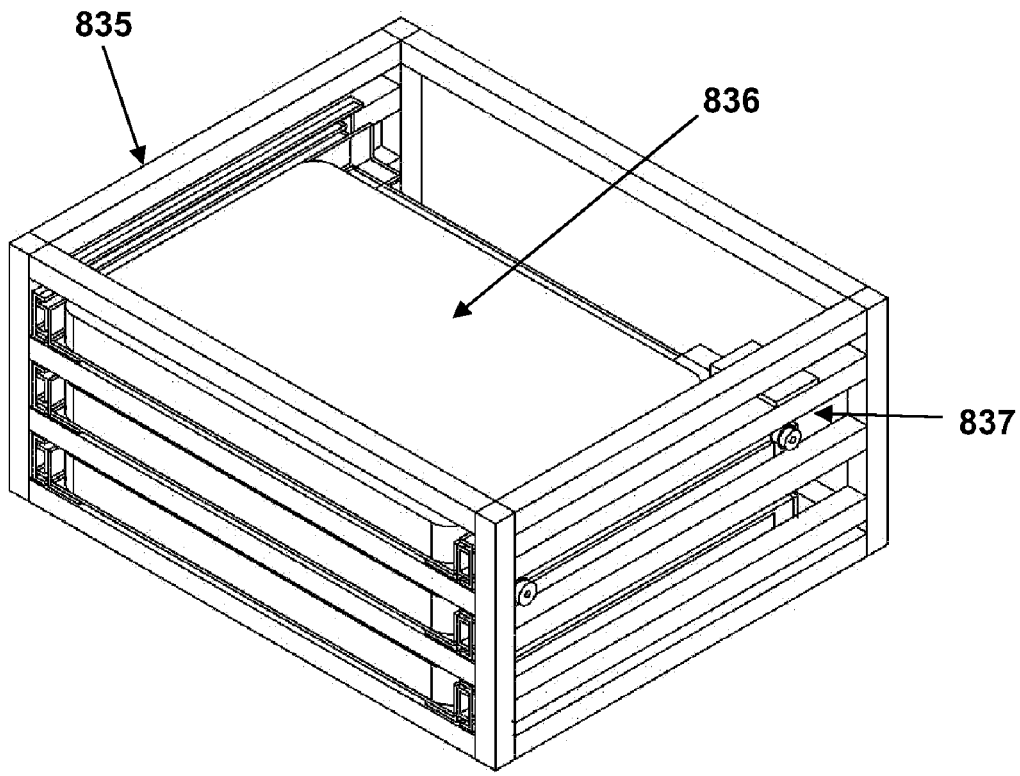
FIG. 8 illustrates an exemplary robot-ready storage cabinet for use in the system of FIG. 1, which enables a robot to store and retrieve spare instruments during reloading.

An exemplary robot-ready storage cabinet (see FIG. 2B, 216) is a spares cache accessible by the robot. A perspective view of the robot-ready storage cabinet is shown in FIG. 8. It is comprised of a metal frame 835 holding a number of motorized drawers 836. Each drawer contains a insert preloaded with spare instruments. A motor on each drawer 837 can be actuated to open the drawer. The control software maintains a database of the spares located in each drawer and can actuate a particular drawer to open when a particular spare is needed. When open, the drawers are within the robot's operation envelope (See FIG. 2B, 203). After opening the proper drawer, the control software commands the robotic arm to retrieve the needed spare from the appropriate slot using the process described in "Unloading/Reloading Robot-Ready Slots" above. The control software then commands the drawer closed.

Although various embodiments of the present invention have been described with reference to a particular arrangement of parts, features and the like, these are not intended to exhaust all possible arrangements or features, and indeed many other embodiments, modifications and variations will be ascertainable to those of skill in the art.

SUMMARY

Along with the claimed invention, the application provides the following features:

A method for processing a plurality of surgical instruments for cleaning, comprising the steps of:
 identifying an insert having a predetermined configuration for accepting at least one type of surgical instrument;
 identifying each type of a plurality of surgical instruments using an optical apparatus;
 orienting each of the identified surgical instrument types using an automated apparatus;
 placing each of the surgical instrument types in one or more predetermined areas of the insert using the automated apparatus, wherein each area of the insert is configured to accept one type of surgical instrument.

The method wherein the optical apparatus is a machine-vision device.

The method wherein the plurality of surgical instruments are identified according to at least one of (1) size, (2) shape, and (3) color.

The method wherein the automated apparatus comprises a robotic arm.

The method wherein the surgical instrument types are placed in the insert according to a predetermined loading plan.

The method wherein one predetermined area of the insert comprises one or more stringers for accepting looped surgical instruments.

The method wherein one predetermined area of the insert comprises one or more pegs for accepting surgical instruments.

A method for processing a plurality of surgical instruments for cleaning, comprising the steps of
 identifying an insert having a predetermined configuration for accepting at least one type of surgical instrument;
 identifying each type of a plurality of surgical instruments using an electrical apparatus;
 orienting each of the identified surgical instrument types using an automated apparatus;
 placing each of the surgical instrument types in one or more predetermined areas of the insert using the automated apparatus, wherein each area is configured to accept one type of surgical instrument.

The method wherein the electrical apparatus is one of an RFID reader, and a barcode reader.

The method wherein the automated apparatus comprises a robotic arm.

The method wherein the surgical instrument types are placed in the insert according to a predetermined loading plan.

The method wherein one predetermined area of the insert comprises one or more stringers for accepting looped surgical instruments.

The method wherein one predetermined area of the insert comprises one or more pegs for accepting surgical instruments.

A system for processing a plurality of surgical instruments for cleaning, comprising:
 a device for identifying an insert, wherein the insert has a predetermined configuration for accepting at least one type of surgical instrument;
 an optical apparatus for identifying each type of a plurality of surgical instruments;
 an automated apparatus for orienting each of the identified surgical instrument types, and placing each of the surgical instrument types in one or more predetermined areas of the insert, wherein each area of the insert is configured to accept one type of surgical instrument.

The system wherein the optical apparatus is a machine-vision device.

The system wherein the plurality of surgical instruments are identified according to at least one of (1) size, (2) shape, and (3) color.

The system wherein the automated apparatus comprises a robotic arm.

The system wherein the surgical instrument types are placed in the insert according to a predetermined loading plan.

The system wherein one predetermined area of the insert comprises one or more stringers for accepting looped surgical instruments.

The system wherein one predetermined area of the insert comprises one or more pegs for accepting surgical instruments.

A system for processing a plurality of surgical instruments for cleaning, comprising the steps of
 a device for identifying an insert, wherein the insert has a predetermined configuration for accepting at least one type of surgical instrument;
 an apparatus for electrically identifying each type of a plurality of surgical instruments;

an automated apparatus for orienting each of the identified surgical instrument types, and placing each of the surgical instrument types in one or more predetermined areas of the insert, wherein each area of the insert is configured to accept one type of surgical instrument.

The system wherein the apparatus is one of an RFID reader and a barcode reader.

The system wherein the automated apparatus comprises a robotic arm.

The system wherein the surgical instrument types are placed in the insert according to a predetermined loading plan.

The system wherein one predetermined area of the insert comprises one or more stringers for accepting looped surgical instruments.

The system wherein one predetermined area of the insert comprises one or more pegs for accepting surgical instruments.

A method of processing a plurality of surgical instruments for packaging, comprising the steps of:
- identifying an insert containing a plurality of surgical instruments in one or more predetermined areas, wherein each predetermined area correlates to a type of surgical instrument;
- removing and identifying each of the plurality of surgical instruments from the predetermined areas using an automated apparatus;
- orienting each of the plurality of instruments according to type; and
- performing a maintenance process on each of the oriented surgical instruments, wherein the maintenance process comprises at least one of (1) inspecting the physical characteristics of one or more surgical instruments using an optical apparatus, (2) inspecting the mechanical characteristics of one or more surgical instruments using an automated mechanical apparatus, and (3) accessing an instrument inspection record database.

The method wherein the automated apparatus comprises a robotic arm.

The method wherein the insert is identified using one of an RFID reader and a barcode reader.

The method wherein the instruments are oriented using a flipping device that rotationally directs an instrument to turn 180°.

The method wherein the instruments are oriented using the automated apparatus.

The method wherein the optical apparatus is a machine-vision device.

The method wherein the machine-vision device inspects the surgical instrument for one or more of (1) deformation, (2) contamination, and (3) sharpness.

The method wherein the automated mechanical apparatus comprises a device that exerts and measures force applied to the surgical instrument.

The method wherein the step of accessing an instrument inspection record comprises accessing a maintenance history record for an identified surgical instrument to determine if maintenance is required at the time of inspection.

An instrument manipulation device, comprising:
a body;
an actuator; and
two jaws having contoured faces configured on the body of the device, and coupled to the actuator, the contoured face for each jaw comprising a raised surface, wherein the raised surface on one jaw is arranged to oppose the other, wherein the jaws and actuator are configured to manipulate the contoured faces in a predetermined direction.

An instrument flipping device, comprising:
a body;
an actuator;
a drivetrain mounted on the body and coupled to the actuator;
a first plate fixed to a first of two concentric axles of the drivetrain; and
a second plate fixed to a second of the two concentric axles, wherein the first and second plate are radially offset from their respective axles by a predetermined distance.

The robot-ready tray insert wherein the contoured body is perforated.

The robot-ready tray insert wherein the contoured body is configured to allow at least one other insert to be stacked on top of the robot-ready insert.

What is claimed is:

1. A system for processing a plurality of surgical instruments for packaging, comprising:
    an automated apparatus for identifying an insert containing a plurality of surgical instruments in one or more predetermined areas, wherein each predetermined area correlates to a type of surgical instrument, and wherein the automated apparatus removes and identifies each of the plurality of surgical instruments from the predetermined areas; and a device for orienting each of the plurality of instruments according to type
    wherein the automated apparatus performs a maintenance process on each of the oriented surgical instruments, wherein the maintenance process comprises at least one of (1) inspecting the physical characteristics of one or more surgical instruments using an optical apparatus, (2) inspecting the mechanical characteristics of one or more surgical instruments using an automated mechanical apparatus, and (3) accessing an instrument inspection record database.

2. The system according to claim 1, wherein the automated apparatus comprises a robotic arm.

3. The system according to claim 1, wherein the insert is identified using one of an RFID reader and a barcode reader.

4. The system according to claim 1, wherein the device for orienting comprises a flipping device that rotationally directs an instrument to turn 180°.

5. The system according to claim 1, wherein the optical apparatus is a machine-vision device.

6. The system according to claim 5, wherein the machine-vision device inspects the surgical instrument for one or more of (1) deformation, (2) contamination, and (3) sharpness.

7. The system according to claim 1, wherein the automated mechanical apparatus comprises a device that exerts and measures force applied to the surgical instrument.

8. The system according to claim 1, comprising: a body;
an actuator; and
two jaws having contoured faces configured on the body of the device, and coupled to the actuator, the contoured face for each jaw comprising a raised surface, wherein the raised surface on one jaw is arranged to oppose the other, wherein the jaws and actuator are configured to manipulate the contoured faces in a predetermined direction.

9. The system according to claim 1, comprising: a body;
an actuator;
a drivetrain mounted on the body and coupled to the actuator;

a first plate fixed to a first of two concentric axles of the drivetrain; and a second plate fixed to the second of the two concentric axles, wherein the first and second plate are radially offset from their respective axles by a predetermined distance.

10. The system according to claim 1, wherein accessing an instrument inspection record comprises accessing a maintenance history record for an identified surgical instrument to determine if maintenance is required at the time of the maintenance process.

11. A method of processing a plurality of surgical instruments for packaging, comprising the steps of:

identifying an insert containing a plurality of surgical instruments in one or more predetermined areas, wherein each predetermined area correlates to a type of surgical instrument;

removing and identifying each of the plurality of surgical instruments from the predetermined areas using an automated apparatus;

orienting each of the plurality of instruments according to type; and performing a maintenance process on each of the oriented surgical instruments, wherein the maintenance process comprises at least one of (1) inspecting the physical characteristics of one or more surgical instruments using an optical apparatus, (2) inspecting the mechanical characteristics of one or more surgical instruments using an automated mechanical apparatus, and (3) accessing an instrument inspection record database.

* * * * *